(12) United States Patent
McFarland et al.

(10) Patent No.: US 12,239,359 B2
(45) Date of Patent: *Mar. 4, 2025

(54) ELECTROSURGICAL SEAL AND DISSECTION SYSTEMS

(71) Applicant: Applied Medical Resources Corporation, Rancho Santa Margarita, CA (US)

(72) Inventors: Daniel McFarland, Dana Point, CA (US); Michael Whitlock, Irvine, CA (US); Patrick Elliott, Rancho Santa Margarita, CA (US); Duy Nguyen, Rancho Santa Margarita, CA (US); Aaron Jimenez, Rancho Santa Margarita, CA (US); Andrea Chan, Rancho Santa Margarita, CA (US); Vanna Lee, Trabuco Canyon, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 1217 days.

This patent is subject to a terminal disclaimer.

(21) Appl. No.: 17/013,052

(22) Filed: Sep. 4, 2020

(65) Prior Publication Data

US 2020/0397501 A1 Dec. 24, 2020

Related U.S. Application Data

(63) Continuation of application No. 15/334,102, filed on Oct. 25, 2016, now Pat. No. 10,792,092, which is a (Continued)

(51) Int. Cl.
*A61B 18/14* (2006.01)
*A61B 18/12* (2006.01)
(Continued)

(52) U.S. Cl.
CPC ...... *A61B 18/1445* (2013.01); *A61B 18/1206* (2013.01); *A61B 18/1233* (2013.01);
(Continued)

(58) Field of Classification Search
CPC ............ A61B 18/1445; A61B 18/1206; A61B 18/1233; A61B 2018/00607; A61B 2018/00702; A61B 2018/0075
See application file for complete search history.

(56) References Cited

U.S. PATENT DOCUMENTS 371,664 A 10/1887 Brannan et al.
702,472 A 6/1902 Pignolet
(Continued)

FOREIGN PATENT DOCUMENTS

DE 40 24 636 A1 2/1992
DE 40 24 636 C2 12/1992
(Continued)

OTHER PUBLICATIONS

Bertil Vallfors and Bjorn Bergdahl, Automatically controlled bipolar electrocoagulation—"COA-COMP", Neurosurg. Rev., 1984, pp. 187-190.
(Continued)

*Primary Examiner* — Thomas A Giuliani
*Assistant Examiner* — Christine A Dedoulis
(74) *Attorney, Agent, or Firm* — Patrick Ikehara

(57) ABSTRACT

A bipolar electrosurgical fusion/sealer and dissector is provided that is arranged to simultaneously fuse and cut tissue captured between jaws of the instrument. The jaws include particularly positioned, shaped and/or oriented electrodes along with a compressible landing pad to perform the simultaneous fusion and cutting of tissue. An electrosurgical generator is arranged to supply RF energy through the instrument and monitors a phase angle of the supplied RF
(Continued)

energy and adjusts or terminates the supplied RF energy based on the monitored phase angle to optimally fuse and dissect the tissue.

18 Claims, 20 Drawing Sheets

Related U.S. Application Data continuation of application No. PCT/US2015/033546, filed on Jun. 1, 2015.

(60) Provisional application No. 62/004,980, filed on May 30, 2014, provisional application No. 62/005,009, filed on May 30, 2014.

(51) Int. Cl.
*A61B 18/00* (2006.01)
*A61B 90/00* (2016.01)

(52) U.S. Cl.
CPC ............ *A61B 2018/00607* (2013.01); *A61B 2018/00702* (2013.01); *A61B 2018/0075* (2013.01); *A61B 2018/00767* (2013.01); *A61B 2018/00827* (2013.01); *A61B 2018/00869* (2013.01); *A61B 2018/00875* (2013.01); *A61B 2018/00892* (2013.01); *A61B 2018/1452* (2013.01); *A61B 2090/0818* (2016.02)

(56) References Cited

U.S. PATENT DOCUMENTS

| | | |
|---|---|---|
| 728,883 A | 5/1903 | Downes |
| 1,586,645 A | 6/1926 | Bierman |
| 1,935,289 A | 11/1933 | Evans |
| 2,002,594 A | 5/1935 | Wappler et al. |
| 2,031,682 A | 2/1936 | Wappler et al. |
| 2,113,246 A | 4/1938 | Wappler |
| 2,176,479 A | 10/1939 | Willis |
| 2,305,156 A | 12/1942 | Grubel |
| 2,632,661 A | 3/1953 | Cristofv |
| 2,827,056 A | 3/1958 | Degelman |
| 3,085,566 A | 4/1963 | Tolles |
| 3,459,187 A | 8/1969 | Pallotta |
| 3,494,363 A | 2/1970 | Jackson |
| 3,588,710 A | 6/1971 | Masters |
| 3,651,811 A | 3/1972 | Hildebrandt et al. |
| 3,685,518 A | 8/1972 | Beuerle et al. |
| 3,780,416 A | 12/1973 | Rider |
| 3,826,263 A | 7/1974 | Cage et al. |
| 3,911,766 A | 10/1975 | Fridolph et al. |
| 3,920,021 A | 11/1975 | Hiltebrandt |
| 3,938,527 A | 2/1976 | Rioux et al. |
| 3,963,030 A | 6/1976 | Newton |
| 3,970,088 A | 7/1976 | Morrison |
| 3,980,085 A | 9/1976 | Ikuno |
| 3,987,795 A | 10/1976 | Morrison |
| 4,030,501 A | 6/1977 | Archibald |
| 4,041,952 A | 8/1977 | Morrison, Jr. et al. |
| 4,043,342 A | 8/1977 | Morrison, Jr. |
| 4,060,088 A | 11/1977 | Morrison, Jr. et al. |
| 4,074,718 A | 2/1978 | Morrison, Jr. |
| 4,089,336 A | 5/1978 | Cage et al. |
| 4,092,986 A | 6/1978 | Schneiderman |
| 4,094,320 A | 6/1978 | Newton et al. |
| 4,114,623 A | 9/1978 | Meinke et al. |
| 4,126,137 A | 11/1978 | Archibald |
| 4,154,240 A | 5/1979 | Ikuno et al. |
| 4,171,700 A | 10/1979 | Farin |
| 4,181,131 A | 1/1980 | Ogui |
| 4,188,927 A | 2/1980 | Harris |
| 4,196,734 A | 4/1980 | Harris |
| 4,198,957 A | 4/1980 | Cage et al. |
| 4,198,960 A | 4/1980 | Utsugi |
| 4,200,104 A | 4/1980 | Harris |
| 4,231,372 A | 11/1980 | Newton |
| 4,237,887 A | 12/1980 | Gonser |
| 4,244,371 A | 1/1981 | Farin |
| 4,325,374 A | 4/1982 | Komiya |
| 4,331,149 A | 5/1982 | Gonser |
| 4,338,940 A | 7/1982 | Ikuno |
| 4,352,156 A | 9/1982 | Gyugyi |
| 4,370,980 A | 2/1983 | Lottick |
| 4,416,276 A | 11/1983 | Newton et al. |
| 4,416,277 A | 11/1983 | Newton et al. |
| 4,427,014 A | 1/1984 | Bel et al. |
| 4,429,694 A | 2/1984 | McGreevy |
| 4,463,759 A | 8/1984 | Garito et al. |
| 4,487,489 A | 12/1984 | Takamatsu |
| 4,514,619 A | 4/1985 | Kugelman |
| 4,522,206 A | 6/1985 | Whipple et al. |
| 4,552,143 A | 11/1985 | Lottick |
| 4,569,131 A | 2/1986 | Faulk et al. |
| 4,569,345 A | 2/1986 | Manes |
| 4,590,934 A | 5/1986 | Malis et al. |
| 4,599,553 A | 7/1986 | Brennen et al. |
| 4,630,218 A | 12/1986 | Hurley |
| 4,632,109 A | 12/1986 | Paterson |
| 4,644,950 A | 2/1987 | Valli |
| 4,651,280 A | 3/1987 | Chang et al. |
| 4,655,216 A | 4/1987 | Tischer |
| 4,657,018 A | 4/1987 | Hakky |
| 4,658,815 A | 4/1987 | Farin et al. |
| 4,658,819 A | 4/1987 | Harris et al. |
| 4,658,820 A | 4/1987 | Klicek |
| 4,674,498 A | 6/1987 | Stasz |
| 4,685,459 A | 8/1987 | Koch et al. |
| 4,699,146 A | 10/1987 | Sieverding |
| 4,712,545 A | 12/1987 | Honkanen |
| 4,716,897 A | 1/1988 | Noguchi et al. |
| 4,727,874 A | 3/1988 | Bowers et al. |
| 4,739,759 A | 4/1988 | Rexroth et al. |
| 4,741,334 A | 5/1988 | Irnich |
| 4,752,864 A | 6/1988 | Clappier |
| 4,754,757 A | 7/1988 | Feucht |
| 4,788,977 A | 12/1988 | Farin et al. |
| 4,802,476 A | 2/1989 | Noerenberg et al. |
| 4,818,954 A | 4/1989 | Flachenecker et al. |
| 4,827,927 A | 5/1989 | Newton |
| 4,848,335 A | 7/1989 | Manes |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,872,456 A | 10/1989 | Hasson |
| 4,887,612 A | 12/1989 | Esser et al. |
| 4,889,722 A | 12/1989 | Sheffield et al. |
| 4,903,696 A | 2/1990 | Stasz et al. |
| 4,905,691 A | 3/1990 | Rydell |
| 4,922,903 A | 5/1990 | Welch et al. |
| 4,936,281 A | 6/1990 | Stasz |
| 4,937,254 A | 6/1990 | Sheffield et al. |
| 4,938,761 A | 7/1990 | Ensslin |
| 4,942,313 A | 7/1990 | Kinzel |
| 4,958,539 A | 9/1990 | Stasz et al. |
| 4,969,885 A | 11/1990 | Farin |
| 4,976,711 A | 12/1990 | Parins et al. |
| 5,007,908 A | 4/1991 | Rydell |
| 5,013,312 A | 5/1991 | Parins et al. |
| 5,015,227 A | 5/1991 | Broadwin et al. |
| 5,016,521 A | 5/1991 | Haka |
| 5,026,370 A | 6/1991 | Lottick |
| 5,026,371 A | 6/1991 | Rydell et al. |
| 5,035,696 A | 7/1991 | Rydell |
| 5,038,109 A | 8/1991 | Goble et al. |
| 5,047,026 A | 9/1991 | Rydell |
| 5,047,027 A | 9/1991 | Rydell |
| 5,052,402 A | 10/1991 | Bencini et al. |
| 5,057,107 A | 10/1991 | Parins et al. |
| 5,061,269 A | 10/1991 | Muller |
| 5,062,031 A | 10/1991 | Flachenecker et al. |
| 5,071,419 A | 12/1991 | Rydell et al. |

(56) References Cited

U.S. PATENT DOCUMENTS

| | | |
|---|---|---|
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |
| 5,116,332 A | 5/1992 | Lottick |
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Zieve et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hooven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen et al. |
| 5,403,312 A | 4/1995 | Yates et al. |
| 5,403,342 A | 4/1995 | Tovey et al. |
| 5,405,344 A | 4/1995 | Williamson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Huitema et al. |
| 5,509,916 A | 4/1996 | Taylor |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler, Jr. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |

(56) References Cited

U.S. PATENT DOCUMENTS

| | | |
|---|---|---|
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |
| 5,665,100 A | 9/1997 | Yoon |
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,742 A | 2/1998 | Quinn et al. |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze et al. |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | DiMatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenberger |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble |
| 6,039,736 A | 3/2000 | Platt, Jr. |
| 6,050,996 A | 4/2000 | Schmaltz et al. |
| 6,051,010 A | 4/2000 | DiMatteo et al. |
| 6,053,172 A | 4/2000 | Hovda et al. |
| 6,053,914 A | 4/2000 | Eggers et al. |
| 6,056,746 A | 5/2000 | Goble et al. |

(56) References Cited

U.S. PATENT DOCUMENTS

| | | | |
|---|---|---|---|
| 6,063,050 | A | 5/2000 | Manna et al. |
| 6,063,075 | A | 5/2000 | Mihori |
| 6,063,081 | A | 5/2000 | Mulier et al. |
| 6,063,086 | A | 5/2000 | Benecke et al. |
| 6,066,139 | A | 5/2000 | Ryan et al. |
| 6,068,627 | A | 5/2000 | Orszulak et al. |
| 6,068,647 | A | 5/2000 | Witt et al. |
| 6,070,444 | A | 6/2000 | Lontine et al. |
| 6,074,386 | A | 6/2000 | Goble et al. |
| RE36,795 | E | 7/2000 | Rydell |
| 6,083,191 | A | 7/2000 | Rose |
| 6,086,586 | A | 7/2000 | Hooven |
| 6,090,106 | A | 7/2000 | Goble et al. |
| 6,090,120 | A | 7/2000 | Wright et al. |
| 6,092,722 | A | 7/2000 | Heinrichs et al. |
| 6,093,186 | A | 7/2000 | Goble |
| 6,096,037 | A | 8/2000 | Mulier et al. |
| 6,102,909 | A | 8/2000 | Chen et al. |
| 6,106,521 | A | 8/2000 | Blewett et al. |
| 6,109,268 | A | 8/2000 | Thapliyal et al. |
| 6,110,171 | A | 8/2000 | Rydell |
| 6,113,591 | A | 9/2000 | Whayne et al. |
| 6,113,594 | A | 9/2000 | Savage |
| 6,113,596 | A | 9/2000 | Hooven et al. |
| 6,113,598 | A | 9/2000 | Baker |
| 6,117,152 | A | 9/2000 | Huitema |
| 6,120,501 | A | 9/2000 | Long et al. |
| H1904 | H | 10/2000 | Yates |
| 6,132,429 | A | 10/2000 | Baker |
| 6,135,998 | A | 10/2000 | Palanker |
| 6,139,519 | A | 10/2000 | Blythe |
| 6,139,547 | A | 10/2000 | Lontine et al. |
| 6,142,992 | A | 11/2000 | Cheng et al. |
| 6,152,923 | A | 11/2000 | Ryan |
| 6,159,146 | A | 12/2000 | El Gazayerli |
| 6,162,235 | A | 12/2000 | Vaitekunas |
| 6,165,175 | A | 12/2000 | Wampler et al. |
| 6,168,605 | B1 | 1/2001 | Measamer et al. |
| 6,171,304 | B1 | 1/2001 | Netherly et al. |
| 6,174,308 | B1 | 1/2001 | Goble et al. |
| 6,174,309 | B1 | 1/2001 | Wrublewski et al. |
| 6,179,834 | B1 | 1/2001 | Buysse et al. |
| 6,186,147 | B1 | 2/2001 | Cobb |
| 6,187,003 | B1 | 2/2001 | Buysse et al. |
| 6,187,026 | B1 | 2/2001 | Devlin et al. |
| 6,190,383 | B1 | 2/2001 | Schmaltz et al. |
| 6,190,385 | B1 | 2/2001 | Tom et al. |
| 6,190,386 | B1 | 2/2001 | Rydell |
| 6,193,129 | B1 | 2/2001 | Bittner et al. |
| 6,193,653 | B1 | 2/2001 | Evans et al. |
| 6,193,713 | B1 | 2/2001 | Geistert et al. |
| 6,197,026 | B1 | 3/2001 | Farin et al. |
| 6,203,541 | B1 | 3/2001 | Keppel |
| 6,206,823 | B1 | 3/2001 | Kolata et al. |
| 6,206,844 | B1 | 3/2001 | Reichel et al. |
| 6,206,875 | B1 | 3/2001 | Long et al. |
| 6,206,877 | B1 | 3/2001 | Kese et al. |
| 6,210,403 | B1 | 4/2001 | Klicek |
| 6,210,405 | B1 | 4/2001 | Goble et al. |
| 6,214,003 | B1 | 4/2001 | Morgan et al. |
| 6,214,023 | B1 | 4/2001 | Whipple et al. |
| 6,228,023 | B1 | 5/2001 | Zaslavsky et al. |
| 6,228,055 | B1 | 5/2001 | Foerster et al. |
| 6,228,080 | B1 | 5/2001 | Gines |
| 6,228,081 | B1 | 5/2001 | Goble |
| 6,228,083 | B1 | 5/2001 | Lands et al. |
| 6,234,178 | B1 | 5/2001 | Goble et al. |
| 6,237,604 | B1 | 5/2001 | Burnside et al. |
| 6,238,366 | B1 | 5/2001 | Savage et al. |
| 6,238,392 | B1 | 5/2001 | Long |
| 6,238,393 | B1 | 5/2001 | Mulier et al. |
| 6,242,741 | B1 | 6/2001 | Miller et al. |
| 6,246,912 | B1 | 6/2001 | Sluijter et al. |
| 6,251,106 | B1 | 6/2001 | Becker et al. |
| 6,251,110 | B1 | 6/2001 | Wampler |
| 6,254,623 | B1 | 7/2001 | Haibel, Jr. et al. |
| 6,257,241 | B1 | 7/2001 | Wampler |
| 6,258,085 | B1 | 7/2001 | Eggleston |
| 6,261,286 | B1 | 7/2001 | Goble et al. |
| 6,267,761 | B1 | 7/2001 | Ryan |
| 6,270,497 | B1 | 8/2001 | Sekino et al. |
| 6,273,862 | B1 | 8/2001 | Privitera et al. |
| 6,277,114 | B1 | 8/2001 | Bullivant et al. |
| 6,277,115 | B1 | 8/2001 | Saadat |
| 6,277,117 | B1 | 8/2001 | Tetzlaff et al. |
| 6,280,398 | B1 | 8/2001 | Ritchart et al. |
| 6,280,407 | B1 | 8/2001 | Manna et al. |
| 6,280,441 | B1 | 8/2001 | Ryan |
| 6,283,963 | B1 | 9/2001 | Regula |
| 6,287,344 | B1 | 9/2001 | Wampler |
| 6,293,942 | B1 | 9/2001 | Goble et al. |
| 6,293,945 | B1 | 9/2001 | Parins et al. |
| 6,296,637 | B1 | 10/2001 | Thorne et al. |
| 6,296,640 | B1 | 10/2001 | Wampler et al. |
| 6,298,550 | B1 | 10/2001 | Kirwan, Jr. |
| 6,302,903 | B1 | 10/2001 | Mulier et al. |
| 6,306,131 | B1 | 10/2001 | Hareyama et al. |
| 6,306,134 | B1 | 10/2001 | Goble et al. |
| 6,308,089 | B1 | 10/2001 | von der Ruhr et al. |
| 6,309,400 | B2 | 10/2001 | Beaupre |
| 6,312,426 | B1 | 11/2001 | Goldberg et al. |
| 6,315,777 | B1 | 11/2001 | Comben |
| 6,319,221 | B1 | 11/2001 | Savage et al. |
| 6,322,494 | B1 | 11/2001 | Bullivant et al. |
| 6,322,549 | B1 | 11/2001 | Eggers et al. |
| 6,322,561 | B1 | 11/2001 | Eggers et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,736 | B1 | 12/2001 | Mulier et al. |
| 6,328,751 | B1 | 12/2001 | Beaupre |
| 6,331,181 | B1 | 12/2001 | Tierney et al. |
| 6,334,068 | B1 | 12/2001 | Hacker |
| 6,334,861 | B1 | 1/2002 | Chandler et al. |
| 6,336,926 | B1 | 1/2002 | Goble |
| 6,348,051 | B1 | 2/2002 | Farin et al. |
| 6,352,532 | B1 | 3/2002 | Kramer et al. |
| 6,352,536 | B1 | 3/2002 | Buysse et al. |
| 6,358,248 | B1 | 3/2002 | Mulier et al. |
| 6,358,249 | B1 | 3/2002 | Chen et al. |
| 6,358,267 | B1 | 3/2002 | Murakami |
| 6,361,534 | B1 | 3/2002 | Chen et al. |
| 6,364,877 | B1 | 4/2002 | Goble et al. |
| 6,364,879 | B1 | 4/2002 | Chen et al. |
| 6,371,967 | B1 | 4/2002 | Long et al. |
| D457,958 | S | 5/2002 | Dycus et al. |
| 6,383,183 | B1 | 5/2002 | Sekino et al. |
| 6,387,092 | B1 | 5/2002 | Burnside et al. |
| 6,387,109 | B1 | 5/2002 | Davison et al. |
| 6,391,024 | B1 | 5/2002 | Sun et al. |
| 6,391,025 | B1 | 5/2002 | Weinstein et al. |
| 6,398,779 | B1 | 6/2002 | Buysse et al. |
| 6,398,781 | B1 | 6/2002 | Goble et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,747 | B1 | 6/2002 | Lindemann et al. |
| 6,402,748 | B1 | 6/2002 | Schoenman et al. |
| 6,406,475 | B1 | 6/2002 | Wenzler et al. |
| 6,409,722 | B1 | 6/2002 | Hoey et al. |
| 6,409,724 | B1 | 6/2002 | Penny et al. |
| 6,409,728 | B1 | 6/2002 | Ehr et al. |
| 6,416,486 | B1 | 7/2002 | Wampler |
| 6,416,509 | B1 | 7/2002 | Goble et al. |
| 6,423,057 | B1 | 7/2002 | He et al. |
| 6,423,082 | B1 | 7/2002 | Houser et al. |
| 6,432,118 | B1 | 8/2002 | Messerly |
| 6,436,096 | B1 | 8/2002 | Hareyama |
| 6,440,130 | B1 | 8/2002 | Mulier et al. |
| 6,443,952 | B1 | 9/2002 | Mulier et al. |
| 6,443,968 | B1 | 9/2002 | Holthaus et al. |
| 6,443,970 | B1 | 9/2002 | Schulze et al. |
| 6,451,013 | B1 | 9/2002 | Bays et al. |
| 6,451,018 | B1 | 9/2002 | Lands et al. |

(56) References Cited

U.S. PATENT DOCUMENTS

| | | |
|---|---|---|
| 6,454,764 B1 | 9/2002 | Fleenor et al. |
| 6,454,781 B1 | 9/2002 | Witt et al. |
| 6,454,782 B1 | 9/2002 | Schwemberger |
| 6,458,078 B1 | 10/2002 | Lüdtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shapeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman, III et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B1 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckai et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |

(56) References Cited

U.S. PATENT DOCUMENTS

| | | |
|---|---|---|
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoey et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm et al. |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soll et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban, III |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell et al. |
| 7,041,096 B2 | 5/2006 | Malis et al. |
| 7,041,102 B2 | 5/2006 | Truckai et al. |
| 7,044,948 B2 | 5/2006 | Keppel |
| 7,044,949 B2 | 5/2006 | Orszulak et al. |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess et al. |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus et al. |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross et al. |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich et al. |
| 7,150,748 B2 | 12/2006 | Ebbutt et al. |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey et al. |
| 7,169,145 B2 | 1/2007 | Isaacson et al. |
| 7,169,146 B2 | 1/2007 | Truckai et al. |
| 7,172,591 B2 | 2/2007 | Harano et al. |
| 7,179,254 B2 | 2/2007 | Pendkanti et al. |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol et al. |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah et al. |
| 7,195,630 B2 | 3/2007 | Ciarrocca |
| 7,195,631 B2 | 3/2007 | Dumbauld |
| 7,204,835 B2 | 4/2007 | Latterell et al. |

(56) References Cited

U.S. PATENT DOCUMENTS

| | | |
|---|---|---|
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble et al. |
| 7,214,224 B2 | 5/2007 | Goble |
| 7,216,001 B2 | 5/2007 | Hacker et al. |
| 7,220,260 B2 | 5/2007 | Fleming et al. |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida et al. |
| 7,229,307 B2 | 6/2007 | Ehr et al. |
| 7,232,439 B2 | 6/2007 | Ciarrocca |
| 7,232,440 B2 | 6/2007 | Dumbald et al. |
| 7,235,048 B2 | 6/2007 | Rein et al. |
| 7,235,072 B2 | 6/2007 | Sartor et al. |
| 7,235,073 B2 | 6/2007 | Levine et al. |
| 7,237,708 B1 | 7/2007 | Guy et al. |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses et al. |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham et al. |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanaka et al. |
| 7,354,435 B2 | 4/2008 | Farin et al. |
| 7,354,440 B2 | 4/2008 | Truckai et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Mulier et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton, IV et al. |
| 7,416,437 B2 | 8/2008 | Sartor et al. |
| 7,419,487 B2 | 9/2008 | Johnson et al. |
| 7,422,139 B2 | 9/2008 | Shelton, IV et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kühner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,464,846 B2 | 12/2008 | Shelton, IV et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |
| 7,491,199 B2 | 2/2009 | Goble |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 9,161,813 B2 | 10/2015 | Benamou |
| 2001/0037110 A1 | 11/2001 | Schmaltz et al. |
| 2001/0039417 A1 | 11/2001 | Harano et al. |
| 2002/0052599 A1 | 5/2002 | Goble |
| 2002/0115997 A1 | 8/2002 | Truckai et al. |
| 2002/0120262 A1 | 8/2002 | Bek et al. |
| 2002/0120266 A1 | 8/2002 | Truckai et al. |
| 2002/0128650 A1 | 9/2002 | McClurken |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham et al. |
| 2003/0014052 A1 | 1/2003 | Buysse et al. |
| 2003/0060818 A1 | 3/2003 | Kannenberg et al. |
| 2003/0065327 A1 | 4/2003 | Wellman et al. |
| 2003/0065358 A1 | 4/2003 | Frecker et al. |
| 2003/0069571 A1 | 4/2003 | Treat et al. |
| 2003/0109871 A1 | 6/2003 | Johnson et al. |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus et al. |
| 2003/0199863 A1 | 10/2003 | Swanson et al. |
| 2003/0199870 A1 | 10/2003 | Truckai et al. |
| 2003/0229344 A1 | 12/2003 | Dycus et al. |
| 2003/0236549 A1 | 12/2003 | Bonadio et al. |
| 2004/0006340 A1 | 1/2004 | Latterell et al. |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis et al. |
| 2004/0092922 A1 | 5/2004 | Kadziauskas et al. |
| 2004/0122423 A1 | 6/2004 | Dycus et al. |
| 2004/0162557 A1 | 8/2004 | Tetzlaff et al. |
| 2004/0193148 A1 | 9/2004 | Wham et al. |
| 2004/0215127 A1 | 10/2004 | Kadziauskas et al. |
| 2004/0225288 A1 | 11/2004 | Buysse et al. |
| 2004/0250419 A1 | 12/2004 | Sremich et al. |
| 2005/0004563 A1 | 1/2005 | Racz et al. |
| 2005/0004564 A1 | 1/2005 | Wham et al. |
| 2005/0021027 A1 | 1/2005 | Shields et al. |
| 2005/0033282 A1 | 2/2005 | Hooven |
| 2005/0033352 A1 | 2/2005 | Zepf et al. |

(56) References Cited

U.S. PATENT DOCUMENTS

| | | |
|---|---|---|
| 2005/0080319 A1 | 4/2005 | Dinkler, II et al. |
| 2005/0090815 A1 | 4/2005 | Francischelli et al. |
| 2005/0096681 A1 | 5/2005 | Desinger et al. |
| 2005/0101951 A1 | 5/2005 | Wham et al. |
| 2005/0107785 A1 | 5/2005 | Dycus et al. |
| 2005/0113817 A1 | 5/2005 | Isaacson et al. |
| 2005/0113819 A1 | 5/2005 | Wham et al. |
| 2005/0113827 A1 | 5/2005 | Dumbauld et al. |
| 2005/0124915 A1 | 6/2005 | Eggers et al. |
| 2005/0137592 A1 | 6/2005 | Nguyen et al. |
| 2005/0149017 A1 | 7/2005 | Dycus |
| 2005/0159745 A1 | 7/2005 | Truckai et al. |
| 2005/0165444 A1 | 7/2005 | Hart et al. |
| 2005/0192568 A1 | 9/2005 | Truckai et al. |
| 2005/0203504 A1 | 9/2005 | Wham et al. |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079788 A1 | 4/2006 | Anderson et al. |
| 2006/0079878 A1 | 4/2006 | Houser |
| 2006/0129146 A1 | 6/2006 | Dycus et al. |
| 2006/0161190 A1 | 7/2006 | Gadberry et al. |
| 2006/0167450 A1 | 7/2006 | Johnson et al. |
| 2006/0173453 A1 | 8/2006 | Gruhl et al. |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom et al. |
| 2006/0247498 A1 | 11/2006 | Bonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus et al. |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus et al. |
| 2007/0142834 A1 | 6/2007 | Dumbauld |
| 2007/0156139 A1 | 7/2007 | Schecter et al. |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lischinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture et al. |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D'Amelio et al. |
| 2008/0167651 A1 | 7/2008 | Tetzlaff et al. |
| 2008/0172048 A1 | 7/2008 | Martin et al. |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darian et al. |
| 2009/0012520 A1 | 1/2009 | Hixson et al. |
| 2009/0024126 A1 | 1/2009 | Artale et al. |
| 2009/0171350 A1 | 7/2009 | Dycus et al. |
| 2009/0171352 A1 | 7/2009 | Sutter |
| 2009/0248007 A1* | 10/2009 | Falkenstein ...... A61B 17/07207 606/49 |
| 2009/0270852 A1 | 10/2009 | Takashino et al. |
| 2009/0275490 A1 | 11/2009 | Milne et al. |
| 2009/0275940 A1 | 11/2009 | Malackowski et al. |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0046295 A1 | 2/2013 | Kerr et al. |
| 2013/0138101 A1 | 5/2013 | Kerr |
| 2013/0138102 A1 | 5/2013 | Twomey et al. |
| 2013/0197874 A1 | 8/2013 | Heckel |
| 2013/0267951 A1 | 10/2013 | Twomey |
| 2013/0274743 A1 | 10/2013 | Banfalvi |
| 2013/0296843 A1 | 11/2013 | Boudreaux et al. |
| 2013/0345696 A1 | 12/2013 | Behnke, II et al. |
| 2014/0005658 A1 | 1/2014 | Rosenbegr |
| 2014/0088583 A1 | 3/2014 | Singh |
| 2014/0214019 A1 | 7/2014 | Baxter, III et al. |
| 2016/0058492 A1 | 3/2016 | Yates et al. |
| 2016/0310203 A1 | 10/2016 | Gaspredes et al. |
| 2016/0310204 A1 | 10/2016 | McHenry et al. |

FOREIGN PATENT DOCUMENTS

| | | |
|---|---|---|
| DE | 10 2005 044 918 A1 | 2/2007 |
| EP | 0 315 338 A1 | 5/1989 |
| EP | 0 538 984 A2 | 4/1993 |
| EP | 0 570 675 B1 | 11/1993 |
| EP | 0 598 202 B1 | 5/1994 |
| EP | 0 717 967 A2 | 6/1996 |
| EP | 0 737 447 A1 | 10/1996 |
| EP | 0 878 168 A1 | 11/1998 |
| EP | 1 054 637 B1 | 11/2000 |
| EP | 1 157 666 A1 | 11/2001 |
| EP | 1 500 378 A1 | 1/2005 |
| EP | 1 535 581 A2 | 6/2005 |
| EP | 1 545 361 B1 | 6/2005 |
| EP | 1 557 129 A1 | 7/2005 |
| EP | 1 634 539 A1 | 3/2006 |
| EP | 1 634 539 B1 | 3/2006 |
| EP | 1 665 995 A1 | 6/2006 |
| EP | 1 728 475 A2 | 12/2006 |
| EP | 1 810 628 A1 | 7/2007 |
| EP | 1 946 715 A1 | 7/2008 |
| EP | 2 158 867 A1 | 8/2009 |
| EP | 2 106 762 A1 | 10/2009 |
| EP | 2 111 812 A2 | 10/2009 |
| EP | 2 156 802 A2 | 2/2010 |
| EP | 2 301 462 A1 | 3/2011 |
| EP | 2 340 792 A1 | 7/2011 |
| EP | 2 436 327 A1 | 4/2012 |
| EP | 2 436 330 A1 | 4/2012 |
| EP | 2 574 300 A1 | 4/2013 |
| EP | 2 712 568 A2 | 4/2014 |
| EP | 2 777 578 A1 | 9/2014 |
| EP | 3 369 392 A2 | 9/2018 |
| GB | 2 157 175 A | 10/1985 |
| GB | 2 462 453 A | 8/2008 |
| JP | 60-30946 A | 2/1994 |

(56) References Cited

FOREIGN PATENT DOCUMENTS

| | | |
|---|---|---|
| JP | 83-17935 A | 12/1996 |
| JP | 11-070123 A | 3/1999 |
| JP | 11-070124 A | 3/1999 |
| JP | 11-178833 A | 7/1999 |
| JP | 2000-254135 A | 9/2000 |
| JP | 2003-135481 A | 5/2003 |
| JP | 2003-164463 A | 6/2003 |
| JP | 2006-109945 A | 4/2006 |
| JP | 2006-167403 A | 6/2006 |
| JP | 2007-144201 A | 6/2007 |
| JP | 2007-195980 A | 8/2007 |
| JP | 2007-195985 A | 8/2007 |
| JP | 2008-043789 A | 2/2008 |
| JP | 2008-259864 A | 10/2008 |
| WO | WO 93/015662 A1 | 8/1993 |
| WO | WO 97/010764 A1 | 3/1997 |
| WO | WO 99/040857 A1 | 8/1999 |
| WO | WO 01/012090 A1 | 2/2001 |
| WO | WO 2004/030553 A1 | 4/2004 |
| WO | WO 2004/032776 A1 | 4/2004 |
| WO | WO 2004/032777 A1 | 4/2004 |
| WO | WO 2004/082495 A1 | 9/2004 |
| WO | WO 2005/004735 A1 | 1/2005 |
| WO | WO 05/053785 A2 | 6/2005 |
| WO | WO 2006/119245 A2 | 11/2006 |
| WO | WO 2006/125558 A1 | 11/2006 |
| WO | WO 2007/044849 A1 | 4/2007 |
| WO | WO 2007/142601 A1 | 12/2007 |
| WO | WO 2008/147773 A1 | 12/2008 |
| WO | WO 2009/065140 A1 | 5/2009 |
| WO | WO 2012/110996 A2 | 8/2012 |
| WO | WO 2013/030349 A1 | 3/2013 |

OTHER PUBLICATIONS

"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System," mailed Jul. 27, 2009, 31 pgs.
International Preliminary Examining Authority/US, International Preliminary Report on Patentability for International Application No. PCT/US09/39046, titled "Electrosurgical System," dated Mar. 26, 2010, 18 pgs.
European Patent Office, European Search Report for European Application No. EP 10 19 2593, titled "Electrosurgical System," dated Mar. 21, 2011, 8 pgs.
European Patent Office, European Search Report for European Application No. EP 10 19 2614, titled "Electrosurgical System," dated Apr. 18, 2011, 7 pgs.
European Patent Office, Extended European Search Report for European Application No. EP 10 19 2580, dated Jul. 21, 2011, 6 pgs.
International Preliminary Examining Authority/US, International Preliminary Report on Patentability for International Application No. PCT/US09/39046, titled "Electrosurgical System," dated Jan. 17, 2012, 45 pgs.
European Patent Office, European Search Report for European Patent Application No. 12151288, dated Feb. 10, 2012, 8 pgs.
European Patent Office, The International Search Report and Written Opinion of the International Searching Authority for International Application No. PCT/US2011/054661, mailed Mar. 6, 2012, 23 pgs.
European Patent Office, Supplementary European Search Report for European Patent Application No. 08755322, dated Apr. 18, 2012, 3 pgs.
European Patent Office, Supplementary European Search Report for European Patent Application No. 08755322, dated Jun. 6, 2012, 2 pgs.
European Patent Office, Partial European Search Report for European Patent Application No. 15151398.3, dated Jun. 22, 2015, 9 pgs.

U.S. Appl. No. 12/611,352, filed Nov. 3, 2009, titled Tissue Fusion/Welder Apparatus and Method, now U.S. Pat. No. 8,551,089 issued Oct. 8, 2013.
U.S. Appl. No. 12/183,970, filed Jul. 31, 2008, entitled Bipolar Electrosurgical Scissors, now U.S. Pat. No. 8,226,649 issued Jul. 24, 2012.
U.S. Appl. No. 12/416,128, filed Mar. 31, 2009, entitled Electrosurgical System, now U.S. Pat. No. 8,568,411 issued Oct. 29, 2013.
U.S. Patent Application No. PCT/US09/39046 filed Mar. 31, 2009, entitled Electrosurgical System.
U.S. Appl. No. 12/416,668, filed Apr. 1, 2009, entitled Electrosurgical System, now U.S. Pat. No. 8,562,598 issued Oct. 22, 2013.
U.S. Appl. No. 12/416,695, filed Apr. 1, 2009, entitled Electrosurgical System, now U.S. Pat. No. 8,551,088 issued Oct. 8, 2013.
U.S. Appl. No. 12/416,765, filed Apr. 1, 2009, entitled Electrosurgical System, now U.S. Pat. No. 8,915,910 issued Dec. 23, 2014.
U.S. Appl. No. 12/416,751, filed Apr. 1, 2009, entitled Electrosurgical System, now U.S. Pat. No. 8,579,894 issued Nov. 12, 2013.
The International Bureau of WIPO, The International Preliminary Report on Patentability for International Application No. PCT/US2011/054661, entitled "Electrosurgical Instruments and Connections Thereto," dated Apr. 2, 2013, 10 pgs.
European Patent Office, European Search Report for European Application No. EP 13 17 4814.7, titled "Electrosurgical System," dated Sep. 30, 2013, 4 pgs.
European Patent Office, European Search Report for European Patent Application No. EP 14199708.0, entitled "Electrosurgical System," dated Jul. 10, 2015, 14 pgs.
International Searching Authority/US, The International Search Report and the Written Opinion for International Application No. PCT/US2015/031452, titled "Electrosurgical Fusion Device," mailed Dec. 3, 2015, 27 pgs.
International Searching Authority/US, The International Search Report and the Written Opinion for International Application No. PCT/US2015/066473 titled "Bipolar Electrosurgical Sealer and Divider." mailed Mar. 31, 2016, 13 pgs.
International Searching Authority/US, The International Search Report and the Written Opinion for International Application No. PCT/US2015/033546 titled "Electrosurgical Seal and Dissection Systems." mailed Apr. 22, 2016, 31 pgs.
International Preliminary Examining Authority/US, International Preliminary Report on Patentability for International Application No. PCT/US2015/031452, titled "Electrosurgical System," dated Dec. 1, 2016, 21 pgs.
International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
International Preliminary Examining Authority/US, International Preliminary Report on Patentability for International Application No. PCT/US2019/059909, titled "Electrosurgical System," dated May 27, 2021, 15 pgs.
European Patent Office, Extended European Search Report for European Application No. EP 21215386.0, dated May 24, 2022, 6 pgs.
European Patent Office, Extended European Search Report for European Application No. EP 22212171.7, dated Mar. 21, 2023, 7 pgs.
European Patent Office, Extended European Search Report for European Application No. EP 23154961.9, dated May 22, 2023, 8 pgs.
European Patent Office, Extended European Search Report for European Application No. EP 17207793.5, dated May 16, 2018, 9 pgs.
European Patent Office, Extended European Search Report for European Application No. EP 18165110.0, dated Jun. 13, 2018, 6 pgs.
International Searching Authority/US, The International Search Report and the Written Opinion for International Application No.

(56) References Cited

OTHER PUBLICATIONS

PCT/US2019/049768 titled "Electrosurgical Generator Verification System." mailed Dec. 11, 2019, 19 pgs.
European Patent Office, Extended European Search Report for European Patent No. 19198318.8, entitled, "Bipolar Electrosurgical Sealer and Divider," dated Dec. 17, 2019, 10 pgs.
European Patent Office, Invitation to Pay Additional Fees for International Application No. PCT/US2019/049807, titled "Electrosurgical Generator Control System", mailed Dec. 19, 2019, 16 pgs.
International Searching Authority/US, The International Search Report and the Written Opinion for International Application No. PCT/US2019/049807 titled "Electrosurgical Generator Control System." mailed Feb. 12, 2020, 20 pgs.
International Searching Authority/US, The International Search Report and the Written Opinion for International Application No. PCT/US2019/059909 titled "Electrosurgical System." mailed Apr. 28, 2020, 23 pgs.
International Preliminary Examining Authority/US, International Preliminary Report on Patentability for International Application No. PCT/US2019/049768, titled "Electrosurgical Generator Verification System," dated Mar. 18, 2021, 13 pgs.
International Preliminary Examining Authority/US, International Preliminary Report on Patentability for International Application No. PCT/US2019/049807, titled "Electrosurgical Generator Control System," dated Mar. 18, 2021, 13 pgs.

* cited by examiner

111a S2 Voltage
111b S2 Power
111c Impedance (Ω)
111d Energy (VA*s)
111e Temperature (°C)
111f S2 10 x Iout
111g S2 Phase

| Diameter: 0-2mm | | Diameter: 2-4mm | | Diameter: 4+ mm | |
|---|---|---|---|---|---|
| Mean Burst Pressure (psi) | 12.83 | Mean Burst Pressure (psi) | 16.91 | Mean Burst Pressure (psi) | 13.45 |
| Burst Pressure above 3x Systolic (7psi) | | 96.88% | | | |
| Time | 1.08 | Time | 1.92 | Time | 4.68 |

FIG. 22

ELECTROSURGICAL SEAL AND DISSECTION SYSTEMS

CROSS-REFERENCE TO RELATED APPLICATIONS

This application is a continuation of U.S. patent application Ser. No. 15/334,102, filed Oct. 25, 2016, which is a continuation of International Application No. PCT/US2015/033546, filed Jun. 1, 2015, which claims the benefit of U.S. Provisional Application No. 62/005,009, filed May 30, 2014, and U.S. Provisional Application No. 62/004,980, filed May 30, 2014, the entire disclosures of which are incorporated by reference as if set forth in full herein.

BACKGROUND

The present application relates generally to electrosurgical systems and methods and more particularly relates to an electrosurgical fusion/seal and dissection systems.

Electrosurgical devices or instruments have become available that use electrical energy to perform certain surgical tasks. Typically, electrosurgical instruments are surgical instruments such as graspers, scissors, tweezers, blades, needles that include one or more electrodes that are configured to be supplied with electrical energy from an electrosurgical generator. The electrical energy can be used to coagulate, fuse, or cut tissue to which it is applied.

Electrosurgical instruments typically fall within two classifications: monopolar and bipolar. In monopolar instruments, electrical energy is supplied to one or more electrodes on the instrument with high current density while a separate return electrode is electrically coupled to a patient and is often designed to minimize current density. Monopolar electrosurgical instruments can be useful in certain procedures, but can include a risk of certain types of patient injuries such as electrical burns often at least partially attributable to functioning of the return electrode. In bipolar electrosurgical instruments, one or more electrodes is electrically coupled to a source of electrical energy of a first polarity and one or more other electrodes is electrically coupled to a source of electrical energy of a second polarity opposite the first polarity. Bipolar electrosurgical instruments, which operate without separate return electrodes, can deliver electrical signals to a focused tissue area with reduced risks.

Even with the relatively focused surgical effects of bipolar electrosurgical instruments, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired coagulation or cutting effect upon the application of electrical energy varies based on the tissue type and can also vary based on pressure applied to the tissue by an electrosurgical device. However, it can be difficult for a surgeon to assess how quickly a mass of combined tissue types grasped in an electrosurgical instrument will be fused a desirable amount.

SUMMARY

In accordance with various embodiments, an electrosurgical laparoscopic fusion/sealer and dissector instrument is provided that is configured to simultaneously fuse and cut tissue. In various embodiments, the electrosurgical device or instrument includes a first jaw and a second jaw opposing the first jaw to grasp tissue between the first and second jaws. The first jaw includes an electrode and the second jaw includes an electrode. The electrodes of the first and second jaws are arranged to fuse and cut tissue between the first and second jaws using radio frequency energy with center portions of the first and second jaws facing each other being devoid of an electrode.

In various embodiments, an electrosurgical instrument comprises a first jaw with a first electrode having a first surface area to contact tissue and a second electrode with a second surface area to contact tissue. The first surface area is the equal to the second surface area. The instrument also includes a second jaw opposing the first jaws and coupled to the first jaw to grasp tissue between the first and second jaws. The second jaw includes a third electrode having a third surface area to contact tissue and a fourth electrode having a fourth surface area to contact tissue. The third surface area is equal to the fourth surface area and the fourth surface area is greater than the first surface area. The first and third electrodes are arranged to fuse tissue between the first and second jaws using radio frequency energy on one side of a longitudinal axis and the second and fourth electrodes are arranged to fuse tissue between the first and second jaws using radio frequency energy on an opposing side of a longitudinal axis.

In accordance with various embodiments, an electrosurgical system for simultaneously fusing and cutting tissue is provided. The system in various embodiments comprises an electrosurgical generator and an electrosurgical fusion/sealer and dissector instrument or device. The generator includes an RF amplifier and a controller. The RF amplifier supplies RF energy through a removably coupled electrosurgical instrument, e.g., an electrosurgical fusion and dissector, configured to fuse and cut tissue with only RF energy. The controller is arranged to monitor a phase angle of the supplied RF energy, the controller signaling the RF amplifier to increase voltage of the supplied RF energy when the monitored phase angle is greater than zero and increasing. In various embodiments, the controller signals the RF amplifier to halt the supplied RF energy when the monitored phase angle decreases.

Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

FIG. 22 is a graphical representation of samples of experimental data for an electrosurgical system in accordance with various embodiments of the present invention.

DETAILED DESCRIPTION

Generally, a bipolar electrosurgical fusion/sealer and dissector instrument, device or tool is provided that is arranged to simultaneously fuse and cut tissue captured between jaws of the instrument. The jaws include particularly positioned, shaped and/or oriented electrodes along with a compressible landing pad to optimally perform the simultaneous fusion and cutting of tissue. The bipolar electrosurgical fusion and dissector can also separately fuse or cut tissue. The cutting of tissue in accordance with various embodiments is notably performed without the use of a mechanical cutting blade, the use of a particular or center cut electrode or the shearing forces or movement of a scissor. The instrument in accordance with various embodiments is provided to be used in laparoscopic surgery having a maximum diameter of 5 mm and thus is insertable through a 5 mm trocar.

Additionally, in general, an electrosurgical system is provided that includes an electrosurgical generator and a removably coupled electrosurgical instrument, e.g., a fusion and dissector, that are configured to optimally fuse and cut tissue. The RF energy is supplied by the electrosurgical generator that is arranged to provide the appropriate RF energy to fuse and cut the tissue. The generator in accordance with various embodiments determines the appropriate RF energy and the appropriate manner to deliver the RF energy for the particular connected electrosurgical instrument, the particular tissue in contact with the instrument and/or a particular surgical procedure. Operationally, RF sealing or fusing of tissue between the jaws is provided to decrease sealing time, output voltage, output power and/or thermal spread. As such, efficiently and consistently delivering power to tissue is provided to heat tissue through a range of temperatures at a particular rate that has been found to be optimal for the tissue affect.

Figure 1:
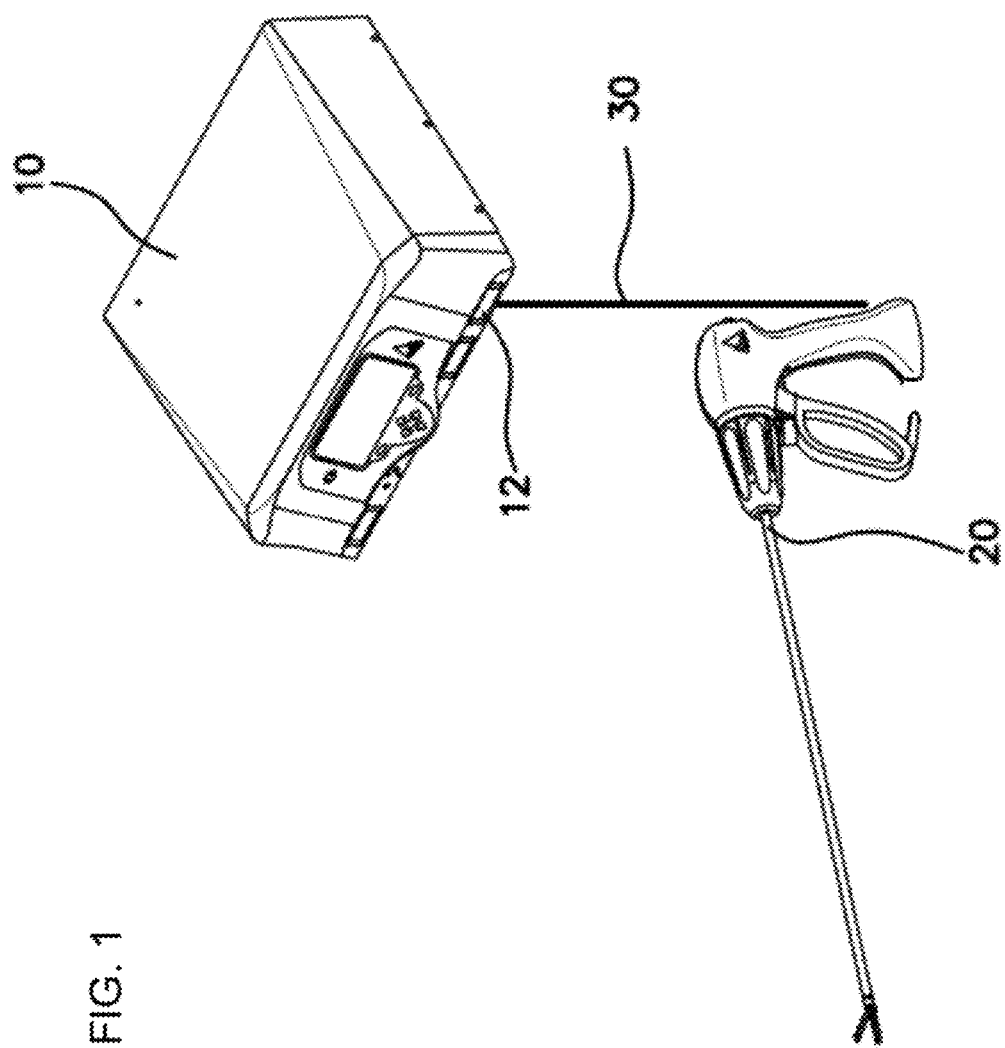
FIG. 1 is a perspective view of an electrosurgical system in accordance with various embodiments of the present invention.
Figure 2:
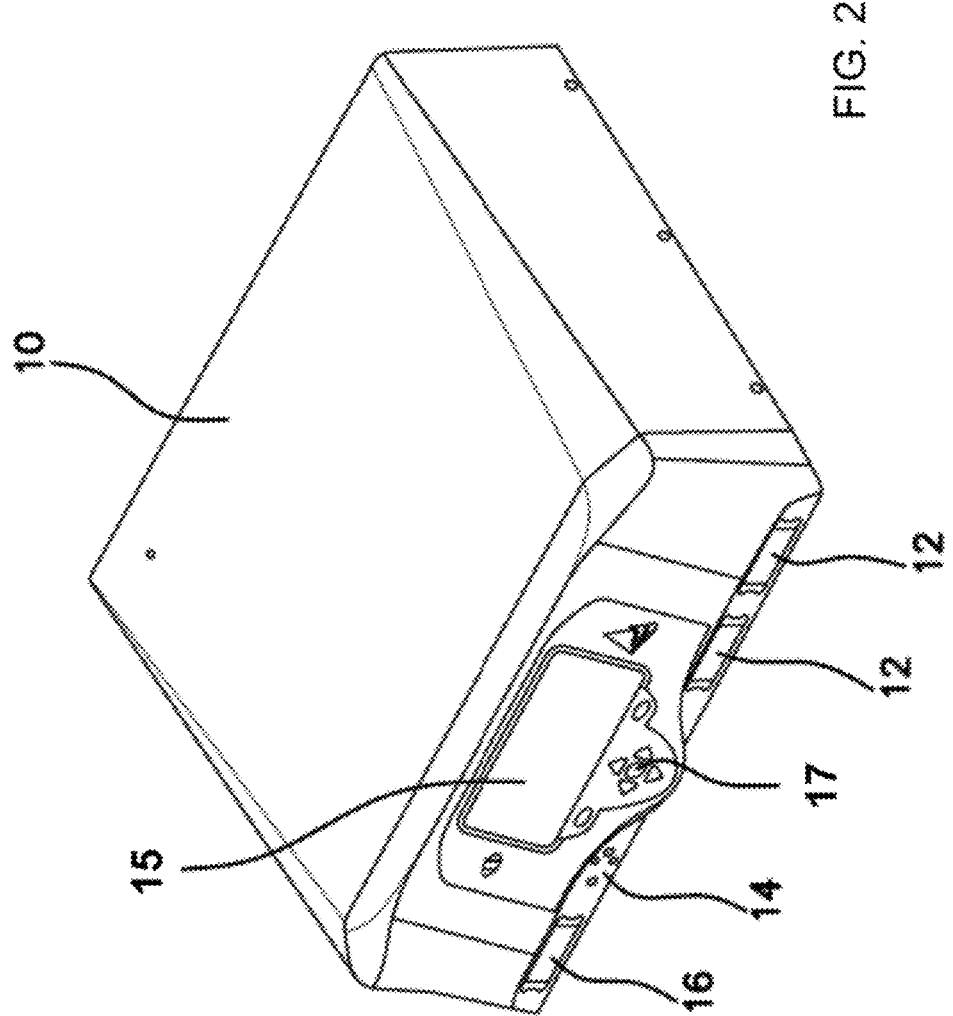
FIG. 2 is a perspective view of an electrosurgical generator in accordance with various embodiments of the present invention.
Figure 3:
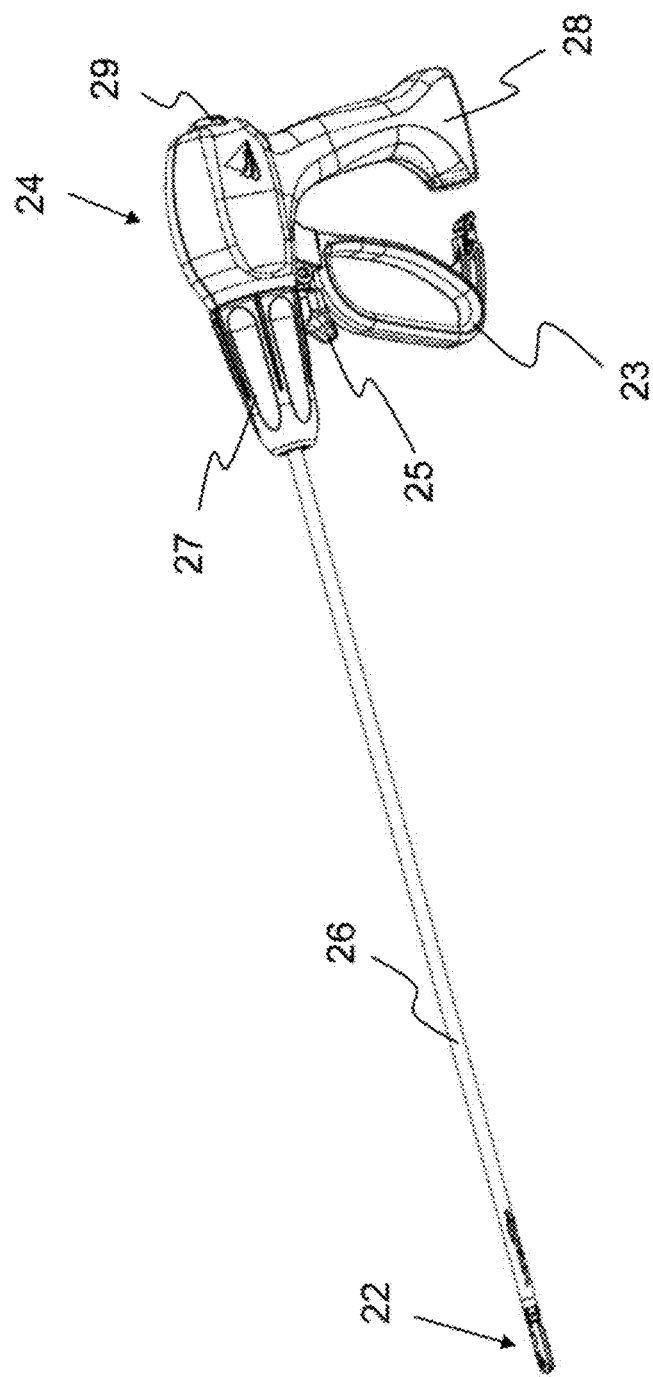
FIG. 3 is a perspective view of an electrosurgical instrument in accordance with various embodiments of the present invention.
Figure 4:
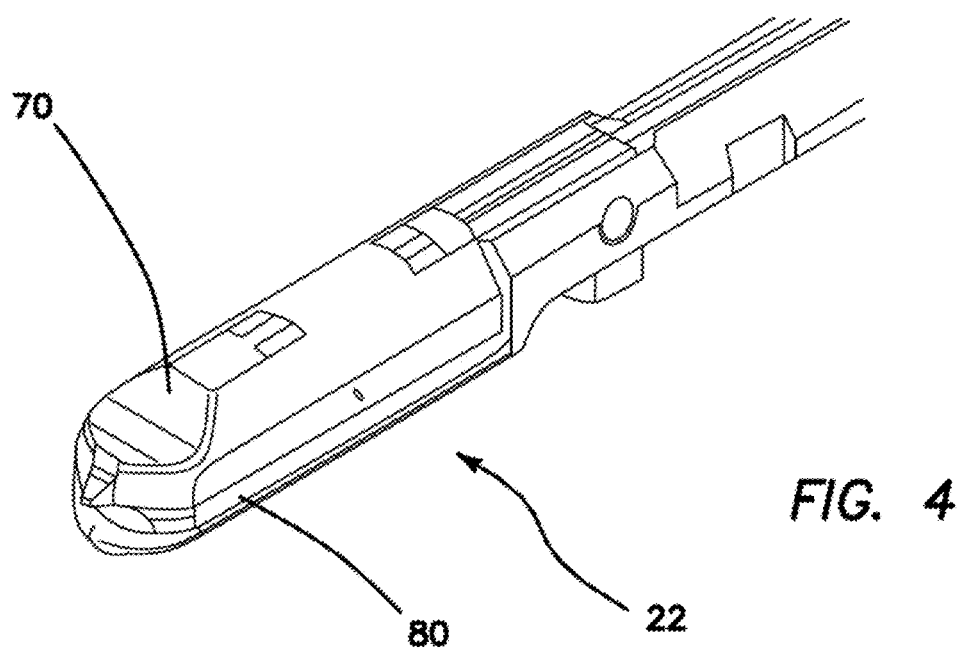
FIG. 4 is a perspective view of a distal end of the electrosurgical instrument in accordance with various embodiments of the present invention.
Figure 5:
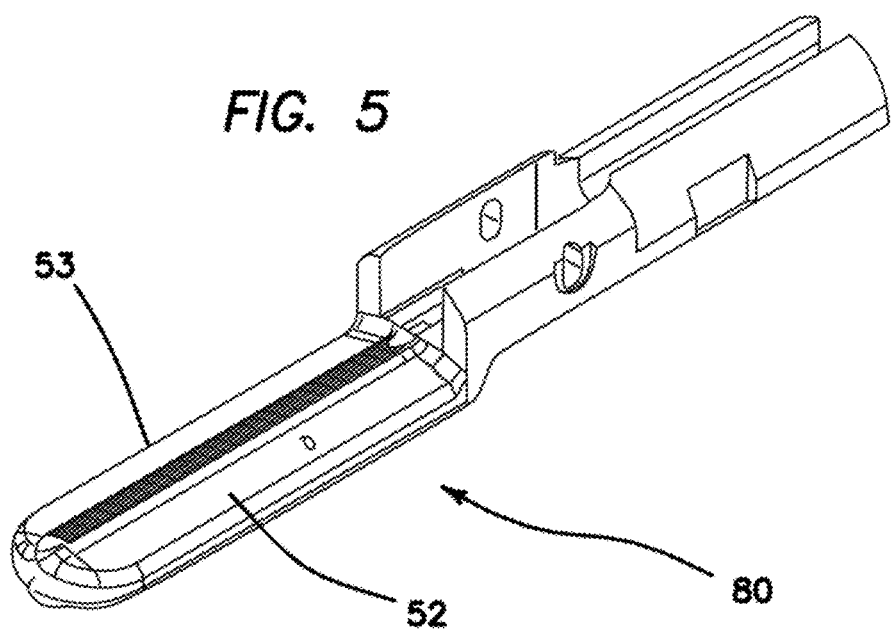
FIG. 5 is a perspective view of a distal end of the electrosurgical instrument in accordance with various embodiments of the present invention.
Figure 6:
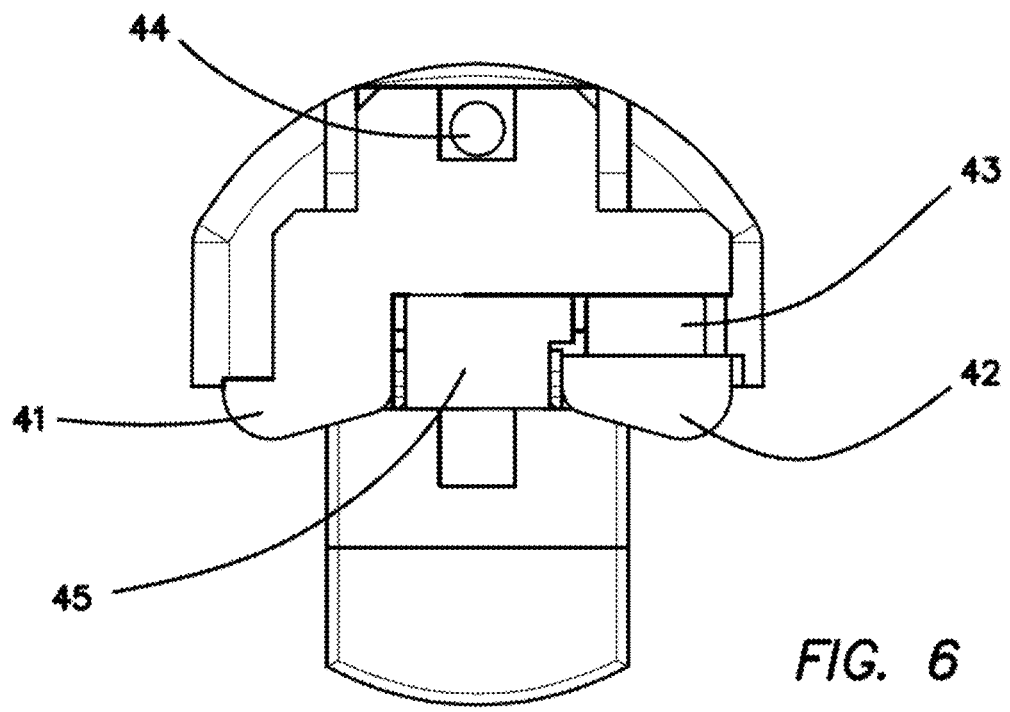
FIG. 6 is a cross-sectional view of a distal end of an electrosurgical instrument in accordance with various embodiments of the present invention.

Referring to FIGS. 1-2, an exemplary embodiment of electrosurgical system is illustrated including an electrosurgical generator 10 and a removably connectable electrosurgical instrument 20. The electrosurgical instrument 20 can be electrically coupled to the generator via a cabled connection 30 to a tool or device port 12 on the generator. The electrosurgical instrument 20 may include audio, tactile and/or visual indicators to apprise a user of a particular predetermined status of the instrument such as a start and/or end of a fusion or cut operation. In other embodiments, the electrosurgical instrument 20 can be reusable and/or connectable to another electrosurgical generator for another surgical procedure. In some embodiments, a manual controller such as a hand or foot switch can be connectable to the generator and/or instrument to allow predetermined selective control of the instrument such as to commence a fusion or cut operation.

In accordance with various embodiments, the electrosurgical generator 10 is configured to generate radiofrequency (RF) electrosurgical energy and to receive data or information from the electrosurgical instrument 20 electrically coupled to the generator. The generator 10 in one embodiment outputs RF energy (e.g., 375 VA, 150V, 5 A at 350 kHz) and in one embodiment is configured to calculate a phase angle or difference between RF output voltage and RF output current during activation or supply of RF energy. The generator regulates voltage, current and/or power and monitors RF energy output (e.g., voltage, current, power and/or phase). In one embodiment, the generator 10 stops RF energy output under predefine conditions such as when a device switch is de-asserted (e.g., fuse button released), a time value is met, and/or active phase angle and/or change of phase is greater than or equal to a phase and/or change of phase stop value.

The electrosurgical generator 10 comprises two advanced bipolar tool ports 12, a standard bipolar tool port 16, and an electrical power port 14. In other embodiments, electrosurgical units can comprise different numbers of ports. For example, in some embodiments, an electrosurgical generator can comprise more or fewer than two advanced bipolar tool ports, more or fewer than the standard bipolar tool port, and more or fewer than the power port. In one embodiment, the electrosurgical generator comprises only two advanced bipolar tool ports.

In accordance with various embodiments, each advanced bipolar tool port 12 is configured to be coupled to electrosurgical instrument having an attached or integrated memory module. The standard bipolar tool port 16 is configured to receive a non-specialized bipolar electrosurgical tool that differs from the advanced bipolar electrosurgical instrument connectable to the advanced bipolar tool port 12. The electrical power port 14 is configured to receive or be connected to a direct current (DC) accessory device that differs from the non-specialized bipolar electrosurgical tool and the advanced electrosurgical instrument. The electrical power port 14 is configured to supply direct current voltage. For example, in some embodiments, the power port 14 can provide approximately 12 Volts DC. The power port 14 can be configured to power a surgical accessory, such as a respirator, pump, light, or another surgical accessory. Thus, in addition to replacing electrosurgical generator for standard or non-specialized bipolar tools, the electrosurgical generator can also replace a surgical accessory power supply. In some embodiments, replacing presently-existing generators and power supplies with the electrosurgical generator can reduce the amount of storage space required on storage racks cards or shelves in the number of mains power cords required in a surgical workspace.

In one embodiment, connection of a non-specialized bipolar tool into the standard bipolar port will not cause the generator to actively check the tool. However, the generator recognizes a connection so that the information of the non-specialized bipolar tool can be displayed. In accordance with various embodiments, the generator recognizes device connection status for each of the advanced tool ports 12 and authenticates connected devices before accepting RF energy activation requests (e.g., activation of an instrument switch such as a fuse button). The generator in one embodiment reads authenticated data from the connected device and reads electrical control values (such as but not limited to voltage level settings, current level settings, power level settings, active phase angle level settings, RF energy output activation timing limits, instrument short limits, instrument open limits, instrument model/identification, RF energy output line configurations, switch state command configurations and/or combinations thereof) from the authenticated and connected device.

In accordance with various embodiments, the electrosurgical generator 10 can comprise a display 15. The display can be configured to indicate the status of the electrosurgical system including, among other information, the status of the one or more electrosurgical instruments and/or accessories, connectors or connections thereto. In some embodiments, the display can comprise a multi-line display capable of presenting text and graphical information such as for example an LCD panel display, which, in some embodiments can be illuminated via backlight or sidelight. In some embodiments, the display can comprise a multi-color display that can be configured to display information about a particular instrument electrically coupled to the electrosurgical generator and a color that corresponds to a particular surgical procedure (such as, for example cutting operations displayed in yellow text and graphics, fusion or welding operations displayed in purple, and coagulation displayed in blue, bloodless dissection operations can be displayed in yellow and blue).

In some embodiments, the display can be configured to simultaneously indicate status data for a plurality of instruments electrically coupled to the electrosurgical generator and/or be portioned to display status information for each instrument connected to a corresponding tool port. A visual indicator such as a status bar graph can be used to illustrate a proportion of total available electrical energy to be applied to the bipolar electrosurgical instrument when actuated. In various embodiments, an electrosurgical instrument operable to cut, seal, coagulate, or fuse tissue could have three color-coded displays or bar graphs. In some embodiments, a user can toggle the display between presenting status of multiple electrically connected instruments and status of a single electrically connected instrument. In accordance with various embodiments, once an instrument and/or accessory is connected and/or detected a window opens in the user interface display showing the type of instrument connected and status.

The electrosurgical generator in accordance with various embodiments can comprise a user interface such as, for example a plurality of buttons 17. The buttons can allow user interaction with the electrosurgical generator such as, for example, requesting an increase or decrease in the electrical energy supplied to one or more instruments coupled to the electrosurgical generator. In other embodiments, the display 15 can be a touch screen display thus integrating data display and user interface functionalities. In accordance with various embodiments, through the user interface, the surgeon can set a voltage setting by the selection of one to three levels. For example, at level 1, voltage is set to 110V; at level 2, voltage is set to 100V; and at level 3, voltage is set to 90V. Current is set to 5 Amps and power is set to 300 VA for all three levels. In other embodiments, the voltage is preset or defaults to a specific level such as level 2. In other embodiments, like the current and power settings, the voltage setting is not user adjustable to simplify operation of the generator and as such a predetermined default voltage setting is utilized, e.g., voltage is set to 100V.

In one embodiment, the electrosurgical tool or instrument 20 can further comprise of one or more memory modules. In some embodiments, the memory comprises operational data concerning the instrument and/or other instruments. For example, in some embodiments, the operational data may include information regarding electrode configuration/reconfiguration, the instrument uses, operational time, voltage, power, phase and/or current settings, and/or particular operational states, conditions, scripts, processes or procedures. In one embodiment, the generator initiate reads and/or writes to the memory module.

In one embodiment, each advanced bipolar electrosurgical instrument comes with a memory module and/or an integrated circuit that provides instrument authentication, configuration, expiration, and logging. Connection of such instruments into the receptacles or ports initiates an instrument verification and identification process. Instrument authentication in one embodiment is provided via a challenge-response scheme and/or a stored secret key also shared by the generator. Other parameters have hash keys for integrity checks. Usages are logged to the generator and/or to the instrument integrated circuit and/or memory. Errors in one embodiment can result in unlogged usage. In one embodiment, the log record is set in binary and interpreted with offline instruments or via the generator.

In one embodiment, the generator uses time measurement components to monitor an instrument's expiration. Such components utilize polling oscillators or timers or real-time calendar clocks that are configured at boot time. Timer interrupts are handled by the generator and can be used by scripts for timeout events. Logging also utilizes timers or counters to timestamp logged events.

In accordance with various embodiments, the generator provides the capability to read the phase difference between the voltage and current of the RF energy sent through the connected electrosurgical instrument while RF energy is active. While tissue is being fused, phase readings are used to detect different states during the fuse or seal and cut process.

In one embodiment, the generator logs usage details in an internal log that is down loadable. The generator has memory for storage of code and machine performance. The generator has reprogrammable memory that contains instructions for specific instrument performance. The memory for example retains a serial number and instrument use parameters. The generator stores information on the type of instruments connected. Such information includes but is not limited to an instrument identifier, e.g., a serial number of a connected instrument, along with a time stamp, number of uses or duration of use of the connected instrument, power setting of each and changes made to the default setting. The memory in one embodiment holds data for about two months, about 10,000 instrument uses or up to 150 logged activations and is configured to overwrite itself as needed.

The generator in accordance with various embodiments does not monitor or control current, power or impedance. The generator regulates voltage and can adjust voltage. Electrosurgical power delivered is a function of applied voltage, current and tissue impedance. The generator through the regulation of voltage can affect the electrosurgical power being delivered. However, by increasing or decreasing voltage, delivered electrosurgical power does not necessarily increase or decrease. Power reactions are caused by the power interacting with the tissue or the state of the tissue without any control by a generator other than by the generator supplying power.

The generator once it starts to deliver electrosurgical power does so continuously, e.g., every 150 ms, until a fault occurs or a specific phase parameter is reached. In one example, the jaws of the electrosurgical instrument can be opened and thus compression relieved at any time before, during and after the application of electrosurgical power. The generator in one embodiment also does not pause or wait a particular duration or a predetermined time delay to commence termination of the electrosurgical energy.

With reference to FIGS. 3-14, in accordance with various embodiments, an bipolar fusion and dissector electrosurgical instrument 20 is provided. In the illustrated embodiment, the instrument 20 includes an actuator 24 coupled to an elongate rotatable shaft 26. The elongate shaft 26 has a proximal end and a distal end defining a central longitudinal axis therebetween. At the distal end of the shaft 26 are jaws 22 and at the proximal end is the actuator. In one embodiment, the actuator is a pistol-grip like handle. The shaft 26 and jaws 22, in one embodiment, are sized and shaped to fit through a 5 mm diameter trocar cannula or access port.

The actuator 24 includes a movable handle 23 and a stationary handle or housing 28 with the movable handle 23 coupled and movable relative to the stationary housing. In accordance with various embodiments, the movable handle 23 is slidably and pivotally coupled to the stationary housing. In operation, the movable handle 23 is manipulated by a user, e.g., a surgeon to actuate the jaws, for example, selectively opening and closing the jaws. In accordance with various embodiments, the actuator 24 includes a force regulation mechanism that is configured such that in a closed configuration, the jaws 22 delivers a gripping force between a predetermined minimum force and a predetermined maximum force.

As part of the force regulation mechanism, the movable handle 23 is coupled to the stationary handle at two sliding pivot locations to form the force regulation mechanism. The movable handle has a first end including a gripping surface formed thereon and a second end opposite the first end. The movable handle is coupled to a pin adjacent the second end. In some embodiments, the movable handle can be integrally formed with a protrusion extending therefrom defining a pin surface, while in other embodiments, a pin can be press-fit into an aperture in the movable handle. The pin can be contained within slots in the stationary housing, such as a corresponding slot formed in a right and/or left handle frames of the stationary housing. In some embodiments, the slots can be configured to define a desired actuation handle path, such as a curved or angled path, as the actuation handle is moved from the first position corresponding to open jaws to a second position corresponding to closed jaws. The force regulation mechanism includes a biasing member such as a tension spring that biases the pin in a proximal direction. In operation, as a predetermined force is exerted on by movement of the movable handle, a biasing force exerted by the spring is overcome, and the second end of the movable handle can translate generally distally, guided by the pin in the slots.

In accordance with various embodiments, the movable handle is slidably and pivotably coupled to the stationary housing 28 at a location between the first and second ends of the actuation handle. An actuation member such as a pull block is coupled to the actuation handle. When the movable handle is moved proximally, the pull block also moves proximally and longitudinally, closing the jaws 22 thereby clamping any tissue between the jaws. The pull block in accordance with various embodiments is rectangular having open top and bottom faces and a closed proximal end. The movable handle extends through the top and bottom faces of the pull block. An edge of the movable handle bears on the proximal end of the pull block such that movement of the movable handle relative to the stationary housing moves the pull block longitudinally. A distal end of the pull block in one embodiment is coupled to an actuation shaft such as a pull tube, bar, or rod, which can extend longitudinally along the elongate shaft 26. Thus, in operation, movement of the movable handle from the first position to the second position translates the pull block longitudinally within the stationary housing, which correspondingly translates the pull tube generally linearly along the longitudinal axis with respect to the elongate shaft 26. Movement of this pull tube can control relative movement of the jaws 22.

In accordance with various embodiments, the actuator 24 includes a latch mechanism to maintain the movable handle 23 in a second position with respect to the stationary housing 28. In various embodiments, the movable handle comprises a latch arm which engages a matching latch contained within stationary handle for holding the movable handle at a second or closed position. The actuator in various embodiments also comprises a wire harness that includes insulated individual electrical wires or leads contained within a single sheath. The wire harness can exit the stationary housing at a lower surface thereof and form part of the cabled connection. The wires within the harness can provide electrical communication between the instrument and the electrosurgical generator and/or accessories thereof.

In accordance with various embodiments, the actuator includes one or more leads attached to rotational coupling clips configured to allow infinite rotation of the shaft. In various embodiments, a switch is connected to a user manipulated activation button 29 and is activated when the activation button is depressed. In one aspect, once activated, the switch completes a circuit by electrically coupling at least two leads together. As such, an electrical path is then established from an electrosurgical generator to the actuator to supply RF energy to the leads attached to the rotational coupling clips.

In one embodiment, the actuator includes a rotation shaft assembly including a rotation knob 27 which is disposed on an outer cover tube of the elongate shaft 26. The rotation knob allows a surgeon to rotate the shaft of the device while gripping the actuator 24. In accordance with various embodiments, the elongate shaft 26 comprises an actuation tube coupling the jaws 22 with the actuator. In various embodiments, the actuation tube is housed within an outer cover tube. While the actuation tube is illustrated as a generally tubular member that can be nested within the outer cover tube, in other embodiments, a non-tubular actuation member can be used, for example, a shaft, a rigid band, or a link, which, in certain embodiments can be positioned within the outer cover tube.

In accordance with various embodiments, attached to the distal end of the outer cover tube is the rotational shaft assembly comprising two mating hubs and a conductive sleeve. The hubs snap together, engaging with the outer cover tube. In other embodiments, the hubs can be of a monolithic construction and configured to interface with mating features on the outer cover tube. The conductive sleeve can be attached to the proximal portion of the assembled hubs after they are attached to the outer cover tube. When the conductive sleeve is attached to the rear of the assembled hubs, the sleeve traps the exposed end of an isolated wire. In the illustrated embodiment, the isolated wire extends from its entrapment point under the conductive sleeve through a slot in the actuation tube and then inside a protective sleeve. The protective sleeve and isolated wire extend distally inside the actuation tube, towards the jaws. In other embodiments, the isolated wire can be formed integrally with a protective sheath and no separate protective sleeve is present in the actuation tube.

Attached to the distal end of the elongate shaft are jaws 22 that comprise a first jaw 70 and a second jaw 80. In one embodiment, a jaw pivot pin pivotally couples the first and second jaws and allows the first jaw to be movable and pivot relative to the second jaw. In various embodiments, one jaw is fixed with respect to the elongate shaft such that the opposing jaw pivots with respect to the fixed jaw between an open and a closed position. In other embodiments, both jaws can be pivotally coupled to the elongate shaft such that both jaws can pivot with respect to each other.

The jaw geometry provides for specific pressure profiles and specific current densities in specific locations to produce the required fusion/seal and dissection effect. Operationally, the temperature required to achieve sealing and division is minimized while the cross linking of proteins within the vascular structure are maximized thereby maximizing the efficacy of the fuse/seal and division of tissue.

In accordance with various embodiments, in order to monitor the temperature of the biological reaction, phase angle and/or the rate of change of the phase angle is monitored. It has been found that the phase angle provides indicators of the temperature of the biological reaction and an indication that the division of the tissue has occurred. In accordance with various embodiments, the device uses bipolar RF energy for electrosurgery for cutting and fusing of tissue between the jaws when opened or closed and/or in contact with the lower jaw when the jaws are open or closed. In one embodiment, temperature of the tissue during the seal and/or division cycle is monitored.

The advanced bipolar electrosurgical device in accordance with various embodiments uses bipolar RF energy for both the sealing or fusing and the division or cutting of tissue. As such, the device maintains cellular structure of tissue adjacent to the area of division while applying the energy required for the division of tissue. Other RF dissection devices use localized arcing or a spark gap to vaporize tissue and achieve dissection. This may be acceptable for straight tissue dissection because the surrounding area is not also intended to be sealed or fused, but is unlike the fusion and dissector devices and systems in accordance with various embodiments of the present invention.

The advanced bipolar electrosurgical device in accordance with various embodiments also accounts for the high heat associated with the vaporization of tissue or tissue dissection. As such, the device in various embodiments uses temperature control to minimize the energy required to achieve tissue division. By minimizing the energy required, the temperature during the reaction is lower and the cellular structure is less likely to be disrupted due to high energy output.

Maintaining the cellular structure of the operating tissue is needed when simultaneously fusing and dissecting or dividing because it is necessary for sealing to occur adjacent to the area of division. The addition of open cut and seal mode also reduces the number of devices or the exchange of devices used in performance of a surgical procedure as such or all such functionality of such individual devices are provided in the single advanced bipolar laparoscopic device.

In various embodiments, the electrosurgical instrument comprises movable jaws able to capture tissue therebetween. In one embodiment, the jaws include one upper jaw that closes onto a static lower jaw. In accordance with various embodiments, the upper jaw includes a rigid upper jaw member 41, an upper conductive pad 42, a rigid insulating pad 43, a wire 44, and a compressible landing pad 45 which are all bound together using an insert molding process and thus is provided as a single structure or assembly as shown in the FIG. 6.

The rigid upper jaw member and the upper conductive pad are both active electrodes which have opposite polarities. The compressible landing pad provides a surface with a specific spring rate to ensure that contact and pressure occurs between the landing pad and the length of the lower jaw. The upper conductive pad 42 is electrically isolated from the rigid upper jaw member 41 by the landing pad 45 and the insulating pad 43. In various embodiments, the upper jaw is made of stainless steel and is more rigid than the landing pad 45. In various embodiments, the landing pad 45 is made of silicone and is more compliant than the upper jaw member 41 or conductive pad 42. In various embodiments, the insulating pad is made of a non-conductive material and is as rigid as or more rigid than the upper jaw member 41 or the conductive pad 42. In various embodiments, the upper jaw member 41 and the conductive pad are made of the same material.

The upper jaw member 41 and the conductive pad have a lower outer surface arranged to be in contact with tissue. The lower surfaces are angled or sloped and mirror images of each other with such positioning or orientation facilitating focused current densities and securement of tissue. The compressible landing pad 45 has a lower surface arranged to be in contact with tissue and/or the lower jaw. The landing pad in the illustrated embodiment is flat and non-parallel relative to the sloped lower surfaces of upper jaw member and the conductive pad 42. The positioning or orientation of the lower surface of the landing pad assists in focusing current densities, securing of tissue and facilitating electrically dissecting of tissue. The spring rate of the landing pad in various embodiments is predetermined to provide optimal pressure or force to cause or facilitate the electrical division of tissue.

Figure 7:
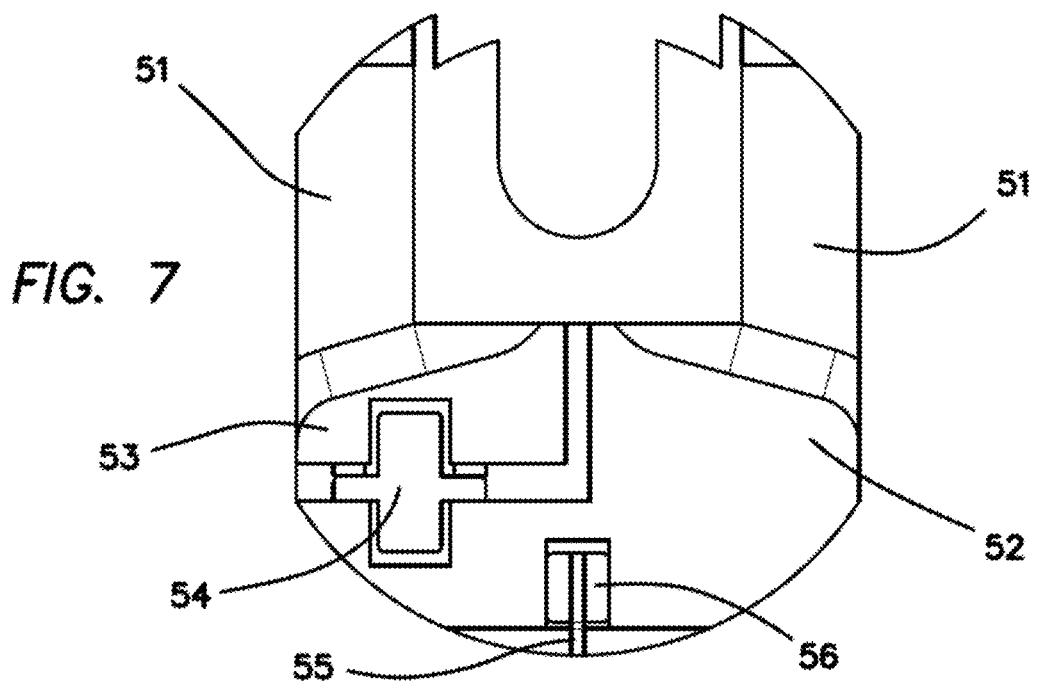
FIG. 7 is a cross-sectional view of a distal end of an electrosurgical instrument in accordance with various embodiments of the present invention.

The lower jaw comprises a rigid lower jaw member 52, a lower conductive pad 53, a cut electrode 55, two rigid insulators 54, 56, as well as two wires, one to the conductive pad and one to the cut electrode, all of which is bound together using an insert molding process and thus are provided as a single structure or assembly as shown in FIG. 7 in accordance with various embodiments of the present invention. The rigid lower jaw member 52, the lower conductive pad 53, and the cut electrode 55 are all or act as active electrodes. The lower conductive pad 53 and the cut electrode 55 have the same polarity and are electrically isolated by the two rigid insulators 54 and 56 from the rigid lower jaw member which has the opposite polarity.

The lower jaw member 52 and the conductive pad 53 have an upper outer surface arranged to be in contact with tissue. The upper surfaces are angled or sloped and mirror images of each other with such positioning or orientation facilitating focused current densities and securement of tissue. In various embodiments, the lower jaw is made of stainless steel and is as rigid as or more rigid than the conductive pad 53. In various embodiments, the rigid insulators 54, 56 are made of a non-conductive material and are as rigid as or more rigid than the lower jaw member 52 or the conductive pad 53. In various embodiments, the lower jaw member 52 and the conductive pad 53 are made of the same material.

Figure 8:
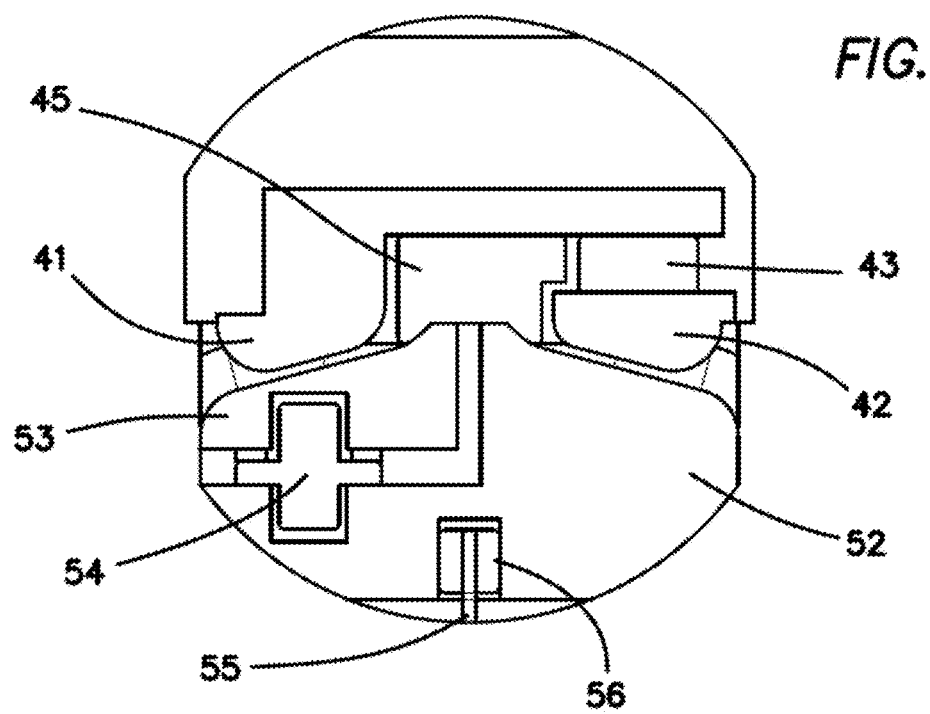
FIG. 8 is a cross-sectional view of a distal end of an electrosurgical instrument in accordance with various embodiments of the present invention.

The overall jaw configuration in accordance with various embodiments is shown in cross-section in FIG. 8 and demonstrates the interaction of the geometries (e.g., shape, dimension, material and any combination thereof for optimal fusion and dissection) between the upper jaw and the lower jaw. In operation, the conductive pads 42, 53 are of the same polarity. The upper and lower jaw members 41, 51, 52 are the same polarity, but the opposite polarity of the conductive pads 42, 53. In one embodiment, the cut electrode 55 is only active during an open cut and fuse operation and is the opposite polarity of the lower jaw member 52. As illustrated, the landing pad 45 interferes and compresses onto the lower jaw member 52 and conductive pad 53 upon closure of the jaws. Tissue (not shown) also captured between the lower jaw and the upper jaw is compressed between the landing pad 45 and the lower jaw member 52 and the conductive pad 53.

Figure 9:
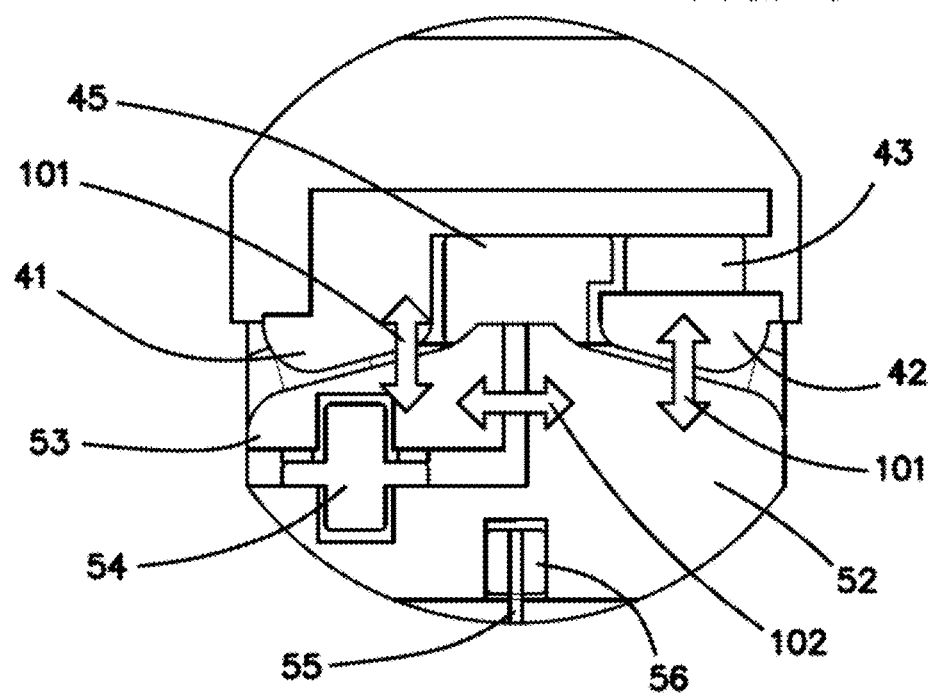
FIG. 9 is a cross-sectional view of a distal end of an electrosurgical instrument in accordance with various embodiments of the present invention.

The polarity of each electrode is set to create the appropriate RF energy and heating due to electrical current passing therebetween. As shown in FIG. 9, the direction of current flow allows for heating between the conductive pads and the jaw members, as well as creating heating from side to side on the lower jaw configuration, as exemplified by arrows 101. The side to side heating on the lower jaw configuration is provided for the division of tissue, as exemplified by arrow 102. In order to divide the tissue down the middle of the jaw, the tissue is heated to reach a temperature between 60° C. and 100° C. to denature the collagen present in the tissue. Once the collagen has been denatured, it enters into a gelatin like state.

Figure 10:
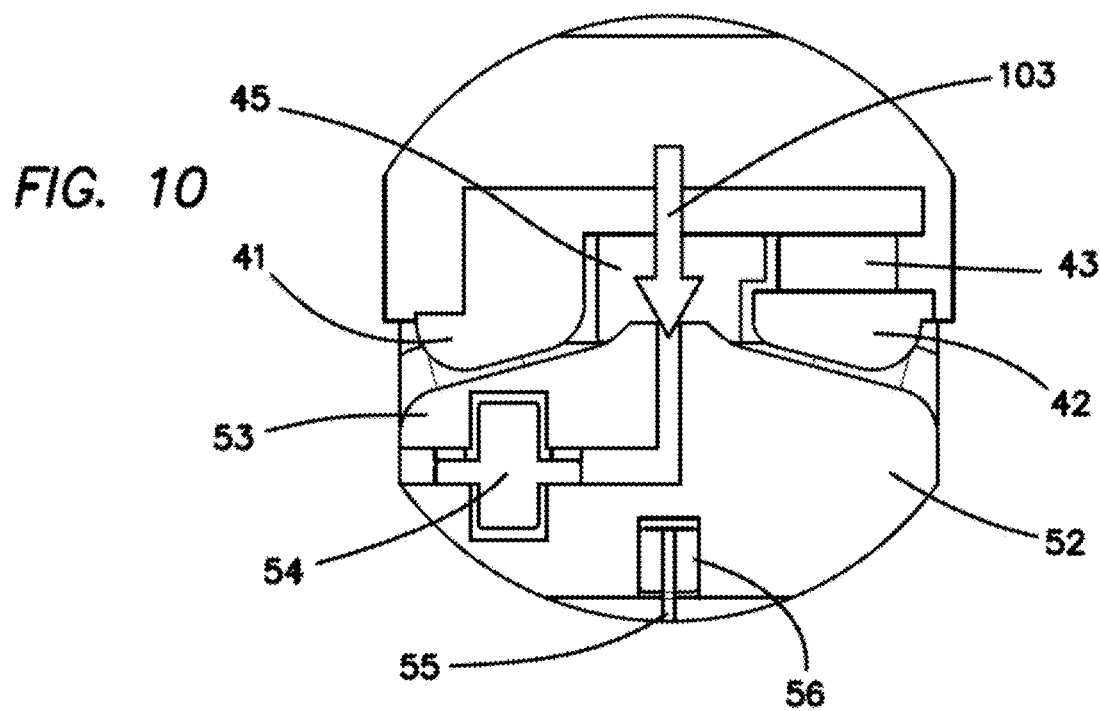
FIG. 10 is a cross-sectional view of a distal end of an electrosurgical instrument in accordance with various embodiments of the present invention.

As the tissue is gelatinous or in a gelatin like state, the spring rate and the interference of the silicone landing pad causes mechanical separation of the tissue as exemplified in FIG. 10 and arrow 103. In various embodiments, the spring rate is predetermined to optimize the separation of the tissue by the interference with the pad and the lower jaw such that the landing pad compresses a predetermined distance or amount in conformance with the tissue there between and with minimal or no effects to the adjacent tissue. Therefore, the configuration of the electrodes allow for simultaneous heating of the seal area (the area between the conductive pads and the jaw members) and the cut area (the side to side current region on the lower jaw). The denaturing of the collagen is also the mechanism used to create a tissue seal or fuse. Sealing utilizes the same temperature (60° C. to 100° C.) as cutting, but the jaw seal spacing between the conductive pads and the jaw members creates a form or mold for the seal to re-cross-link once the RF application ceases. It is noted that reaching high temperatures rapidly can cause the cellular structure to rupture due to the rapid heating of intercellular moisture. Therefore, a gradual increase of temperature and a longer dwell time in the appropriate temperature range allows for more thorough denaturing of the collagen.

Figure 11:
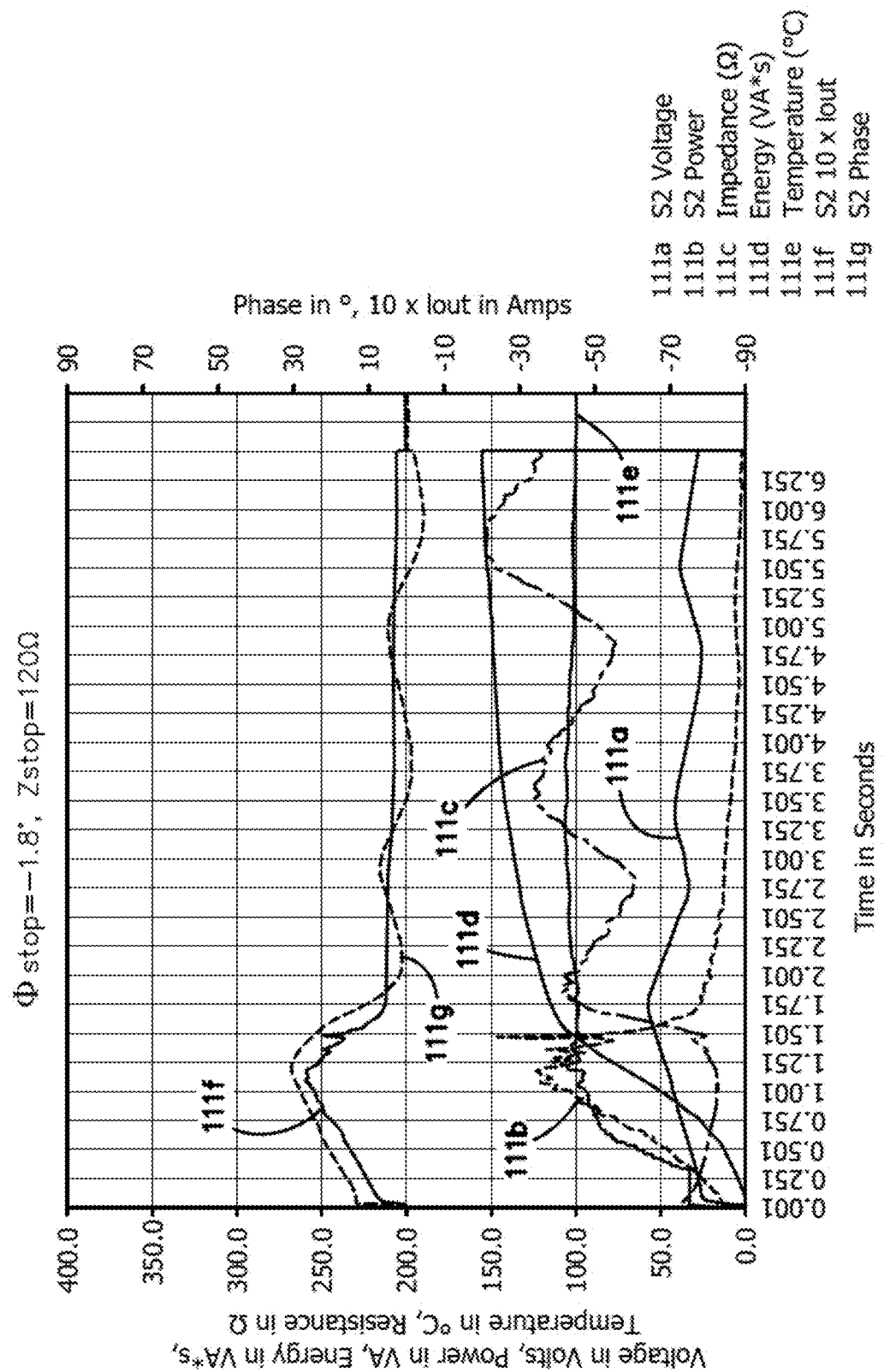
FIG. 11 is a graphical representation of samples of experimental data for a fusion and dissection process with an electrosurgical instrument in accordance with various embodiments of the present invention.
Figure 12:
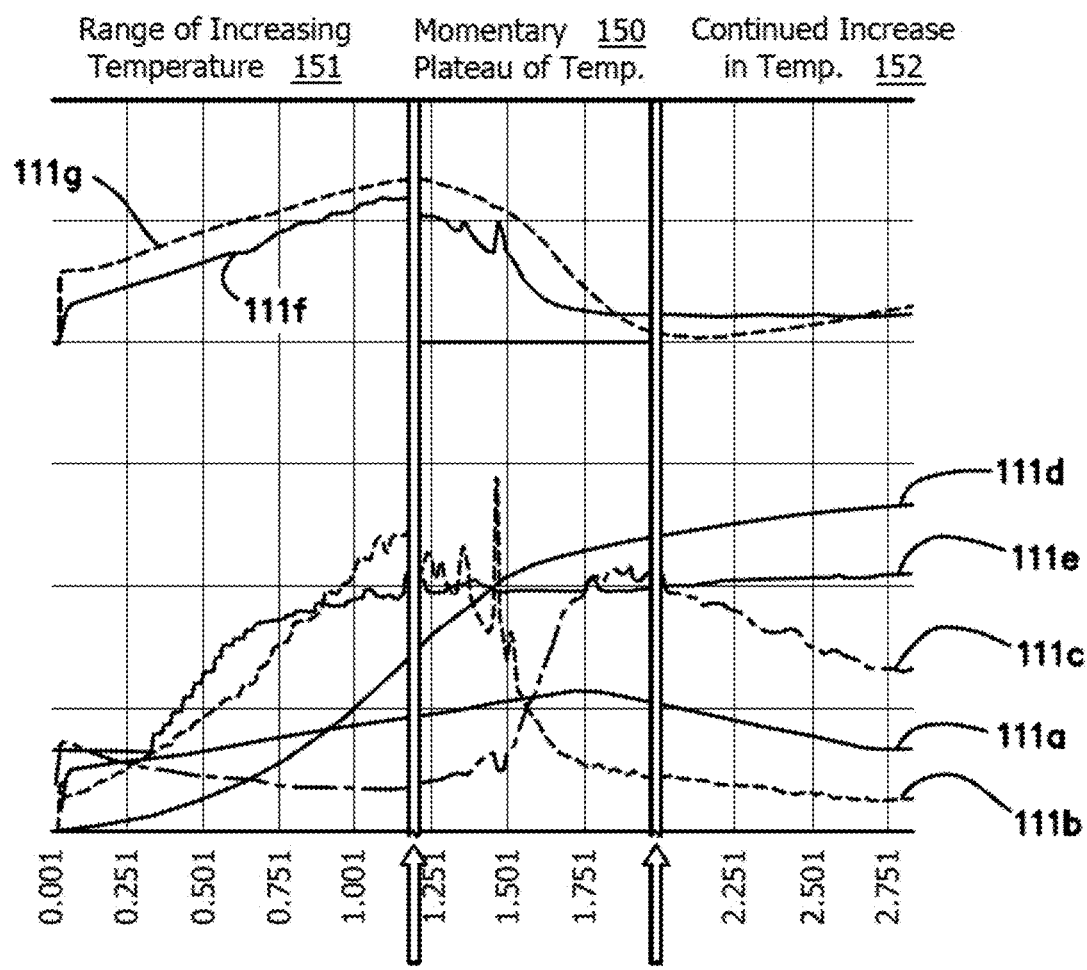
FIG. 12 is a graphical representation of samples of experimental data for a fusion and dissection process with an electrosurgical instrument in accordance with various embodiments of the present invention.
Figure 13:
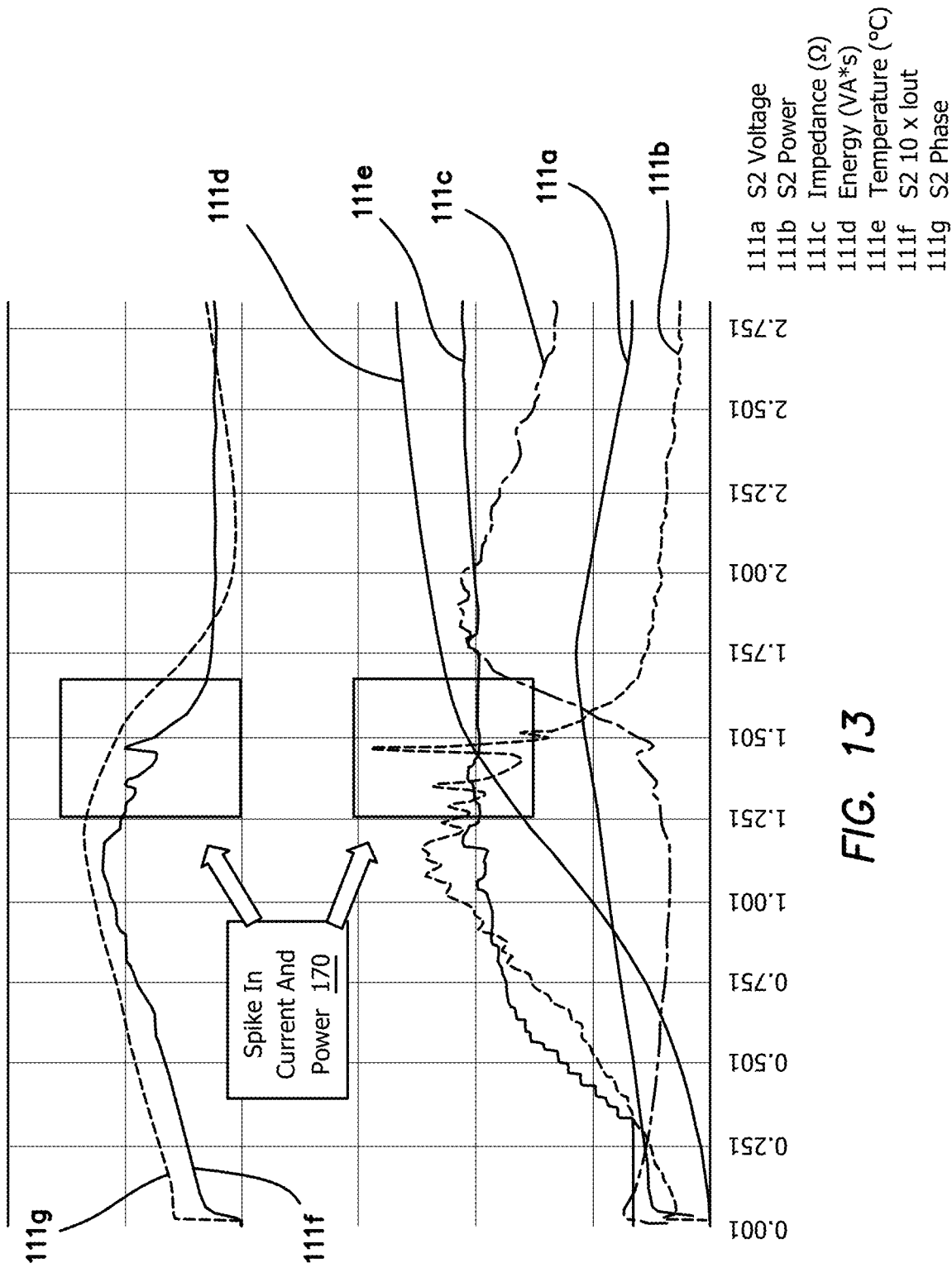
FIG. 13 is a graphical representation of samples of experimental data for a fusion and dissection process with an electrosurgical instrument in accordance with various embodiments of the present invention.

In various embodiments, in order to achieve the appropriate temperature of the tissue to cause the associated tissue effect, e.g., a gradual increase and/or longer dwell time, the phase angle of the tissue and/or the rate of change of the phase angle are monitored. FIGS. 11-13 provide a graphical representation of exemplary seal and division cycles in accordance with various embodiments. Also, as illustrated, phase 111g is shown relative to other tissue readings or indicators such as voltage 111a, power 111b, impedance 111c, energy 111d, temperature 111e and current 111f. Additionally, although shown in FIGS. 11-13, in various embodiments, the generator is configured to not measure or calculate one or more of the indicators or readings, e.g., temperature or energy, to reduce operational and power costs and consumptions and/or the number of parts of the generator. The additional information or readings are generally provided or shown for context purposes.

As shown in FIGS. 11-13, the temperature of the tissue 111e between the jaws increases from the initiation of RF energy to a point of the highest phase angle. At this point of the highest phase angle (or the point of inflection of the rate of change of phase angle) 155 the temperature plateaus 150 momentarily (~0.75 seconds), then continues higher 152, even though voltage decreases.

Due to the behavior of the temperature profile, it is noted that the momentary plateau in temperature may be attributed to the change in state of the water or moisture present in the tissue. When the water begins to boil, the temperature does not increase until the liquid water has been turned to water vapor. The determination of the temperature 111e as such can be based off the phase angle 111g. The temperature prior to the maximum phase angle is associated with a steady heating to 100° C. The plateau in temperature is associated with a sudden decrease in the phase angle which can be associated with 100° C. and two-state water. Because liquid water is highly conductive and water vapor is not, this transition in phase may be another indicator of the water's state. Once the temperature continues to increase past 100° C. (152) and past a second point of phase angle inflection 160, it can be noted that the majority of the water has been turned to water vapor.

Another point of interest that can be seen in the RF output is the sudden spike 170 in power 111b and current 111f during the boiling of water portion of the RF application as shown for example in FIG. 13. The spike can be attributed to the division of the tissue during the sealing or fusing process. This increase in power and current can be due to tissue being no longer present under the insulated portion of the jaws, e.g., the landing pad. At this point, the jaw closes more, and the energy transfer is only through the seal surfaces.

Since the temperature required to denature the collagen begins at 60° C., the energy application is optimized to maximize the time prior to 100° C. This provides for a complete and thorough denaturing of the collagen. As such, all sealing should be completed prior to the spike 170 in power and current such that sealing is completed prior to division.

Figure 14:
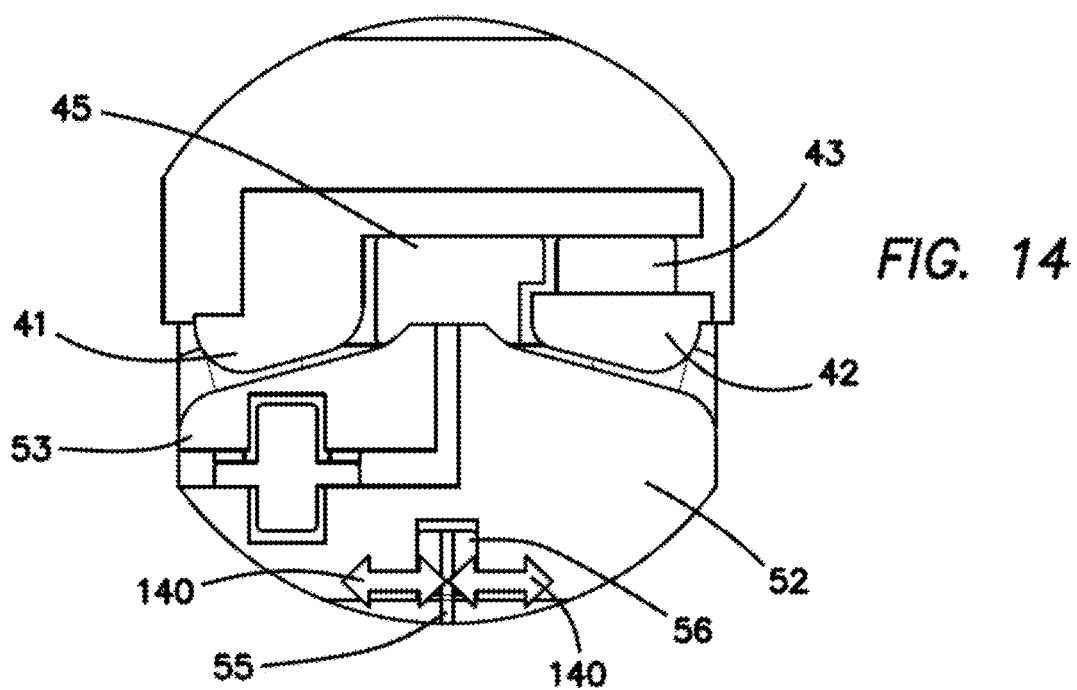
FIG. 14 is a cross-sectional view of a distal end of an electrosurgical instrument in accordance with various embodiments of the present invention.

In accordance with various embodiments, the electrosurgical instrument also has the ability to cut tissue using RF energy and in one embodiment only with the jaws in a fully open position, only utilizing the lower jaw, without cooperation of the upper jaw or tissue not captured between the upper and lower jaws but in contact with the lower jaw. FIG. 14 shows the direction of current flow, arrow 140, from the cut electrode 55 to the rigid lower jaw member 52.

To achieve tissue cutting, a high voltage potential is created between the cut electrode 55 and the lower jaw member 52. This provides for the vaporization of tissue due to the heat created by local arcing around the cut electrode. As high temperature is encountered, the insulating material used to isolate the cut electrode in one embodiment withstands or operates well at high temperatures. Also, with the high voltage potential, the insulator in one embodiment has a high dielectric strength. The voltage potential is greater than 400 V-peak in order to achieve sufficient arcing. The actual potential however is directly related to the spacing between the cut electrode and the lower jaw member.

Arc suppression is another concern and as such quick rectification of RF waveform distortion due to arcing and/or limiting power output to prevent the degradation of the materials used in the construction of the jaw are provided. If an arc is allowed to persist for more than 100 micro seconds, there is an increased risk of device degradation. Also, due to the extreme heat associated with the localized arcing, RF energy application in accordance with various embodiments includes a predetermined duty cycle or a waveform with a high crest factor. It has been found that the crest factor associated with a sinusoidal waveform does not allow for a constant output without causing degradation to the device. Manipulation of the duty cycle or crest factor brings the average output power down over the entire activation of the device.

The electrosurgical instrument in accordance with various embodiments also fuses tissue using RF energy and in one embodiment only with the jaws in a fully open position, only utilizing the lower jaw, without cooperation of the upper jaw or tissue not captured between the upper and lower jaws but in contact with the lower jaw. FIG. 14 exemplarily illustrates a direction of current flow from the cut electrode 55 to the rigid lower jaw member 52.

In accordance with various embodiments, to cause tissue coagulation, a low voltage potential is maintained between the cut electrode 55 and the lower jaw member 52. The voltage potential is set to be lower than 100 V-peak in order to prevent localized arcing, but the actual potential is directly related to the spacing between the cut electrode and the lower jaw member. Tissue coagulation is caused by heat generated by the RF current between the two electrodes.

In one embodiment, the isolated wire 44 is routed to electrically couple the first jaw to the wiring harness in the actuator. The isolated wire extends from the distal end of the protective sleeve which is housed at the proximal end of the second jaw and extends into the first jaw. The first jaw can have a slot positioned to receive the isolated wire. The isolated wire then extends through a hole in the first jaw and drops into a slot in a nonconductive portion. The isolated wire then extends to the distal end of the nonconductive portion and drops through to the conductive pad.

In some embodiments, electrode geometry of or on the conductive pads of the jaws ensures that the sealing area completely encloses the distal portion of the cutting path. In accordance with various embodiments, the dimensions of the jaw surfaces are such that it is appropriately proportioned with regards to the optimal pressure applied to the tissue between the jaws for the potential force the force mechanism can create. Its surface area is also electrically significant with regards to the surface area contacting the tissue. This proportion of the surface area and the thickness of the tissue have been optimized with respect to its relationship to the electrical relative properties of the tissue.

Figure 15:
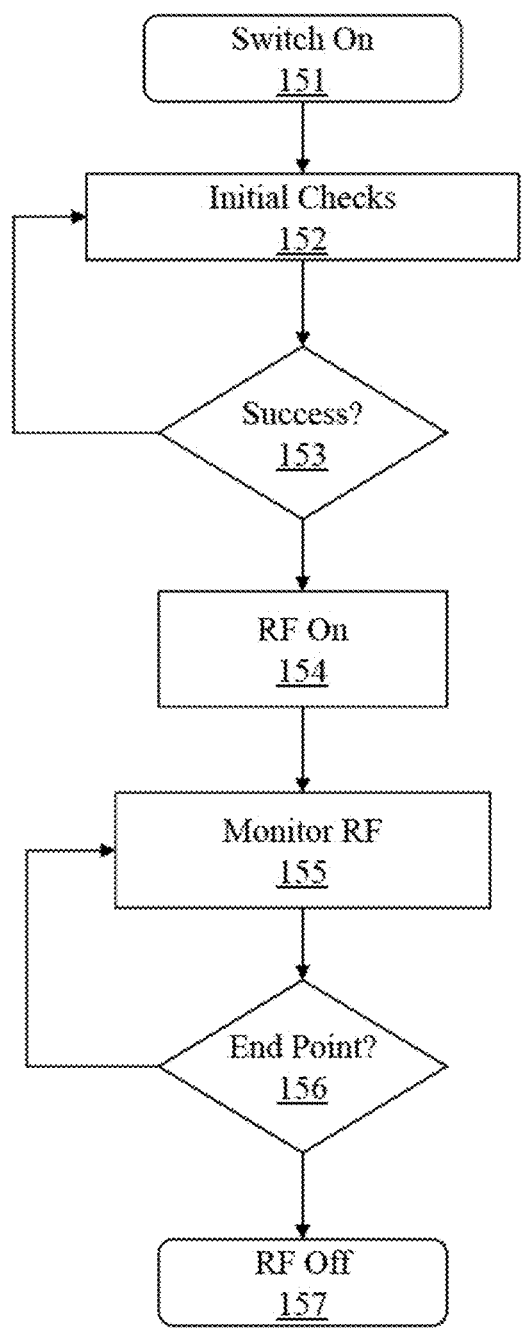
FIG. 15 is a flow chart illustrating operations of an electrosurgical system in accordance with various embodiments of the present invention.

In one embodiment, as illustrated in FIG. 15, an electrosurgical process such as a tissue fusion and/or cut process starts with depressing a switch on the tool (151), which starts an initial measurement sequence. With engagement of a switch on the tool, the generator takes initial measurements on the tissue (opens, shorts, etc.) (152) and based on the initial measurements initiates or does not initiate the supply of RF energy (153). In accordance with various embodiments, the generator measures tool and/or tissue impedance and/or resistance, and/or if a phase angle is within an acceptable range. In one embodiment, the generator performs a passive measurement of tissue between the electrodes of an electrosurgical tool connected to the generator utilizing RF energy with a low energy range (e.g., a voltage about 1-10 Volts) that does not cause a physiological effect. In various embodiments, the generator uses the initial impedance measurement to determine if the tool is shorted, faulty, open and the like. Based on a positive result of the initial check, the generator for example switches-in a supply of RF energy from the generator to the electrosurgical tool and ultimately to the tissue (154). After RF power is turned on and is being supplied continuously by the generator, the generator monitors the phase angle or difference and/or change of phase angle between current and voltage of the supplied RF energy (155).

At or upon a predefined or predetermined point, condition or threshold (156), the supply of RF energy is terminated (157). In this case, an acoustical and/or visual signal is provided indicating that the tissue is fused (or that an error has occurred (e.g., shorting of the electrodes) and/or an unexpected condition has occurred (e.g., permissible although unexpected switch release)). In accordance with various embodiments, the predefined point, condition or threshold and/or initialization checks are determined based on a tool algorithm or script provided for a connected electrosurgical tool, procedure or preference. In accordance with various embodiments, the product of measured tissue permittivity and conductivity or an initial phase shift is utilized to determine the end point for a connected tool.

Figure 16:
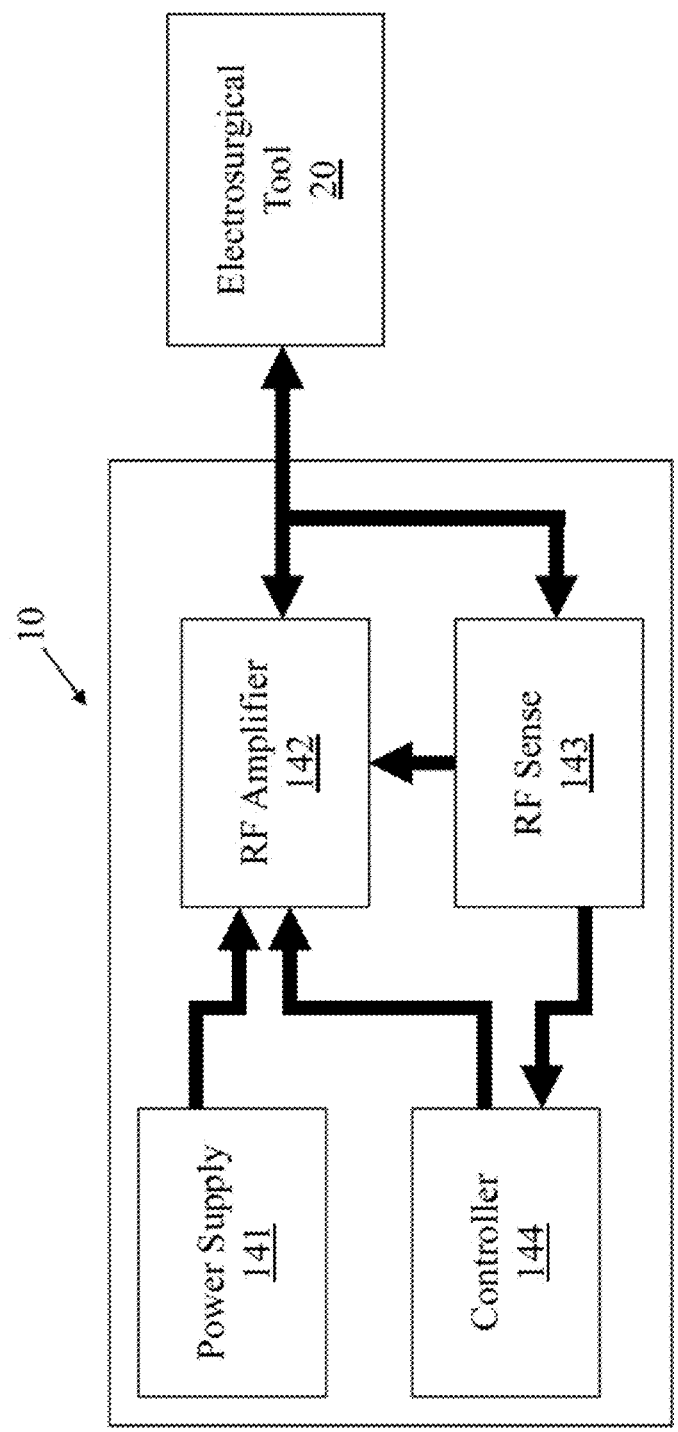
FIG. 16 is a schematic block diagram of portions of an electrosurgical system in accordance with various embodiments of the present invention.

Referring now to FIG. 16, in one embodiment, the electrosurgical generator 10 is connected to AC main input and a power supply 141 converts the AC voltage from the AC main input to DC voltages for powering various circuitry of the generator. The power supply also supplies DC voltage to an RF amplifier 142 that generates RF energy. In one embodiment, the RF amplifier 142 converts 100 VDC from the power supply to a sinusoidal waveform with a frequency of 350 kHz which is delivered through a connected electrosurgical instrument. RF sense circuitry 143 measures/calculates voltage, current, power and phase at the output of the generator in which RF energy is supplied to a connected electrosurgical instrument 20. The measured/calculated information is supplied to a controller 144.

In one embodiment, the RF sense analyzes the measured AC voltage and current from the RF amplifier and generates DC signals for control signals including voltage, current, power, and phase that are sent to the controller for further processing. In one embodiment, RF sense 143 measures the output voltage and current and calculates the root means square (RMS) of the voltage and current, apparent power of the RF output energy and the phase angle between the voltage and current of the RF energy being supplied through a connected electrosurgical instrument. In particular, the voltage and current of the output RF energy are processed by analog circuitry of the RF sense to generate real and imaginary components of both voltage and current. These signals are processed by an field-programmable gate array (FPGA) to give different measurements relating to voltage and current, including the RMS measurements of the AC signals, phase shift between voltage and current, and power. Accordingly, in one embodiment, the output voltage and current are measured in analog, converted to digital, processed by an FPGA to calculate RMS voltage and current, apparent power and phase angle between voltage and current, and then are converted back to analog for the controller.

For each device port there are a pair of signals for voltage and a pair of signals for current that originate from the RF amplifier 142. In one embodiment, the generator has two redundant RF sense circuits 143a, 143b that measures voltage and current for each device at different locations on the RF amplifier. The first RF Sense circuit senses current by sense resistors delivered through a connected electrosurgical instrument on either device port 1 or device port 2, and the voltage measured across return to output on either device port 1 or device port 2. The second RF Sense circuit senses current by sense resistors, returned from a connected electrosurgical instrument on either device port 1 or device port 2, and the voltage 146a, 146b measured across output to return on either device port 1 or device port 2. The voltage input signals are high voltage sinusoidal waveforms at 350 kHz that are attenuated and AC coupled by a voltage divider and an inverting filter to remove DC bias on the signals. An inverting filter is used as the voltage and current inputs are 180 degrees out of phase as they are measured at opposite polarities. For each voltage input signal, two separate inverted and non-inverted voltage sense signals are generated. In one embodiment, a differential voltage measurement is made between the current input signals to generate two separate pairs of inverted and non-inverted current sense signals. The current input signals represent voltage across a shunt resistor on the RF Amplifier in which this voltage is proportional to the current flowing through the shunt resistor. The current input signals are low voltage sinusoidal waveforms at 350 kHz that are amplified using a non-inverting filter to remove DC bias on the signals. The RF Sense generates a signal that is analogous to multiplying each voltage and current signal by predetermined reference signals. As such, the RF Sense provides the non-inverted voltage and current sense signals when the waveform is positive, the inverted voltage and current sense signals when the waveform is negative, and a ground signal when the waveform is zero.

The RF sense in accordance with various embodiments receives four reference synchronization signals supplied by the controller via the RF amplifier. The synchronization signals are 350 kHz pulse signals with the same duty cycle but with differing phase shifts and in one embodiment are 90 degrees phase shifted from each other. Two of the synchronization signals are used to generate the in-phase waveforms to generate the real component of the input waveforms and the two other synchronization signals are used to generate the quadrature waveforms to generate the imaginary components of the input waveforms. These signals are processed further to generate control signals to a plurality of switches. The outputs of the switches are tied together to generate a single output. In one embodiment, the control signals to the switches determine which input signal passes through to the single output. In accordance with various embodiments, a first combination allows non-inverted voltage and current sense signals to pass through which represents or is analogous to multiplying these sense signals by a positive pulse. A second combination allows the inverted voltage and current sense signals to pass through which represents or is analogous to multiplying these sense signals by a negative pulse. A third combination allows the ground signal to pass through generating a zero voltage output which represents or is analogous to multiplying the sense signals by zero. Each output is supplied to a low pass filter that generates a DC voltage corresponding to the real or imaginary component of the sensed signals. These signals are supplied to ADCs which sends a digital signal to the FPGA.

In one embodiment, Controller 144 controls the RF amplifier 142 to affect the output RF energy. For example, Controller utilizes the information provided by the RF sense 143 to determine if RF energy should be outputted and when to terminate the output of RF energy. In one embodiment, the controller compares a predetermined phase threshold based on a particular tissue in contact with the connected electrosurgical device 20 to determine when to terminate the output of RF energy. In various embodiments, the controller performs a fusion process described in greater detail below and in some embodiments the controller receives the instructions and settings or script data to perform the fusion process from data transmitted from the electrosurgical instrument.

Figure 17:
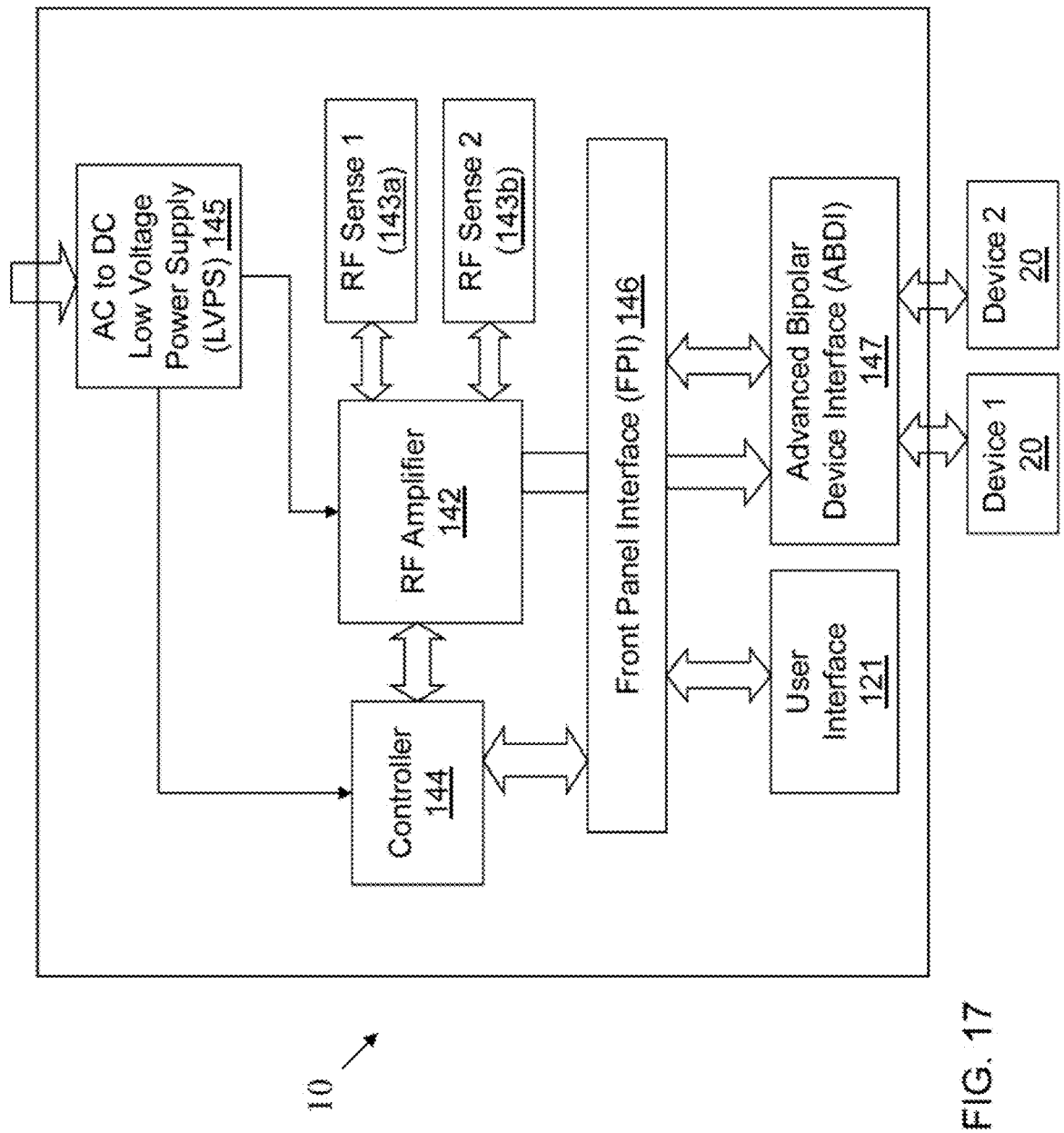
FIG. 17 is a schematic block diagram of portions of an electrosurgical system in accordance with various embodiments of the present invention.

In accordance with various embodiments as shown in FIG. 17, the generator has six major sub-systems or modules of circuitry that include System Power or Power Supply 145, Controller 144, Front Panel Interface 146, Advanced Bipolar Device Interface 147, RF Amplifier 142 and RF Sense 143. In accordance with various embodiments, one or more of the circuitry may be combined or incorporated with other circuitry. The power supply 145 is configured to provide DC voltages to all the other circuitry or sub-systems along with control signals to control the power supply outputs. The power supply receives AC power input that is 90-264 VAC, 47-63 Hz and in one embodiment the power supply has a switch, integrated or separate, that is configured to connect or disconnect the AC power input from the generator. The controller through the Front Panel Interface (FPI) and Advanced Bipolar Device Interface (ABDI) supports the user interface 121 and instrument connections for electrosurgical devices 1 and 2 connected to the electrosurgical generator.

The RF Amplifier 142 generates high power RF energy to be passed through a connected electrosurgical instrument and in one example, an electrosurgical instrument for fusing of tissue. The RF Amplifier in accordance with various embodiments is configured to convert a 100 VDC power source to a high power sinusoidal waveform with a frequency of 350 kHz which is delivered through the ABDI 147 and eventually the connected electrosurgical device. The RF Sense 143 interprets the measured AC voltage and current from the RF amplifier 42 and generates DC control signals, including voltage, current, power, and phase, that is interpreted by Controller 144.

The generator has a plurality of specialized connection receptacles, in the illustrated embodiment device port 1 and device port 2, that are used only for connecting to advanced bipolar devices, such as an advanced bipolar electrosurgical instrument. The specialized receptacles each include an array spring-loaded probes or pogo pins. The generator in various embodiments includes a circuit to detect the presence of an advanced bipolar device prior to energizing any active output terminals at the receptacles.

The Front Panel Interface (FPI) 146 is configured to drive a display, device signals from the controllers and LED backlights for front panel buttons. The FPI is also configured to provide power isolation through regulators and provide functionality for the front panel switches/buttons. In one embodiment, the ABDI 147 is used as a pass-through connection which provides a connection to the devices through the FPI. The FPI also provides connection between Controller 144 and a connected electrosurgical device through the ABDI. The device interface in one embodiment is electrically isolated from the rest of the FPI. The interface in various embodiments includes lines that read and write to an ferromagnetic random access memory (FRAM) on an advanced bipolar device, read a trigger switch and/or read a signal that indicates a device is connected. In one embodiment, a device memory circuit is provided that utilizes the controller's serial peripheral interface (SPI) to read and write the FRAM of the advanced bipolar device. In one embodiment, the FRAM is replaced with a microcontroller and the interface includes an interrupt line so all information passed through a digital interface between the electrosurgical device and the generator. FPI provides isolation for SPI signals to and from advanced bipolar device through ABDI. In one embodiment, the SPI interface is shared between two advanced bipolar devices with port pins being used as chip selects.

In accordance with various embodiments, the generator includes a SPI communication bus that allows the controller to have bi-directional communication with complex programmable logic devices (CPLDs) and the RF Sense FPGAs. In various embodiments, the FPI provides SPI interface between the controller and connected devices through an ABDI connector to communicate with the FRAM on the advanced bipolar devices. FPI also provides electrical isolation for low voltage signals from between controller and the ABDI. The device interface on the ABDI is configured to transmit RF energy to the connected device along with SPI communication. In one embodiment, the ABDI connects a signal from a device that indicates it is connected.

The FPI-ABDI interface provides power to the devices that connect to the generator, SPI communication between controller and the devices, device switch signals from the devices to the controller, and device connected signals from the devices to the controller. ABDI provides the RF energy to each connected advanced bipolar device through a separate pogo pin array. The FPI provides signal, low voltage power and high voltage RF power from the FPI and RF Amplifier to the connected device through the ABDI connector via the pogo pin array.

In accordance with various embodiments, an operations engine enables the generator to be configurable to accommodate different operational scenarios including but not limited to different and numerous electrosurgical tools, surgical procedures and preferences. The operations engine receives and interprets data from an external source to specifically configure operation of the generator based on the received data.

The operations engine receives configuration data from a database script file that is read from a memory device on a device plug. The script defines the state logic used by the generator. Based on the state determined and measurements made by the generator, the script can define or set output levels as well as shutoff criteria. The script in one embodiment includes trigger events that include indications of short condition for example when a measured phase is greater than 70 degrees or an open condition for example when a measured phase is less than −50 degrees.

In one embodiment, the operations engine provides system states and user states. System states are predefined or predetermined states that control or manage specific predefined or predetermined operations of the generator, such as successfully applying RF energy or indicating an error. System states in one embodiment are a pre-defined set of configuration that the system can be in (e.g., idle vs. energized) and whose functions are hard-coded into the electrosurgical generator. For example, a RF Done state is a system state that indicates that an RF energy cycle has been completed without errors. User states provide a framework through which customized or specialized operations and values can be established by direction from an external source for a particular tool, procedure and/or preference.

In one embodiment, the script sets forth the system states and their exit conditions, e.g., expiration times or pointers or directions to another state and where the user states begin. For each user state, operation parameters for the specific state can be defined such as power, voltage, and current settings or are carried over from a previous state. In one embodiment, the user states may provide device, operator or procedural specific states and in one embodiment, the user states may be provided for testing or diagnostics specific states.

Figure 18:
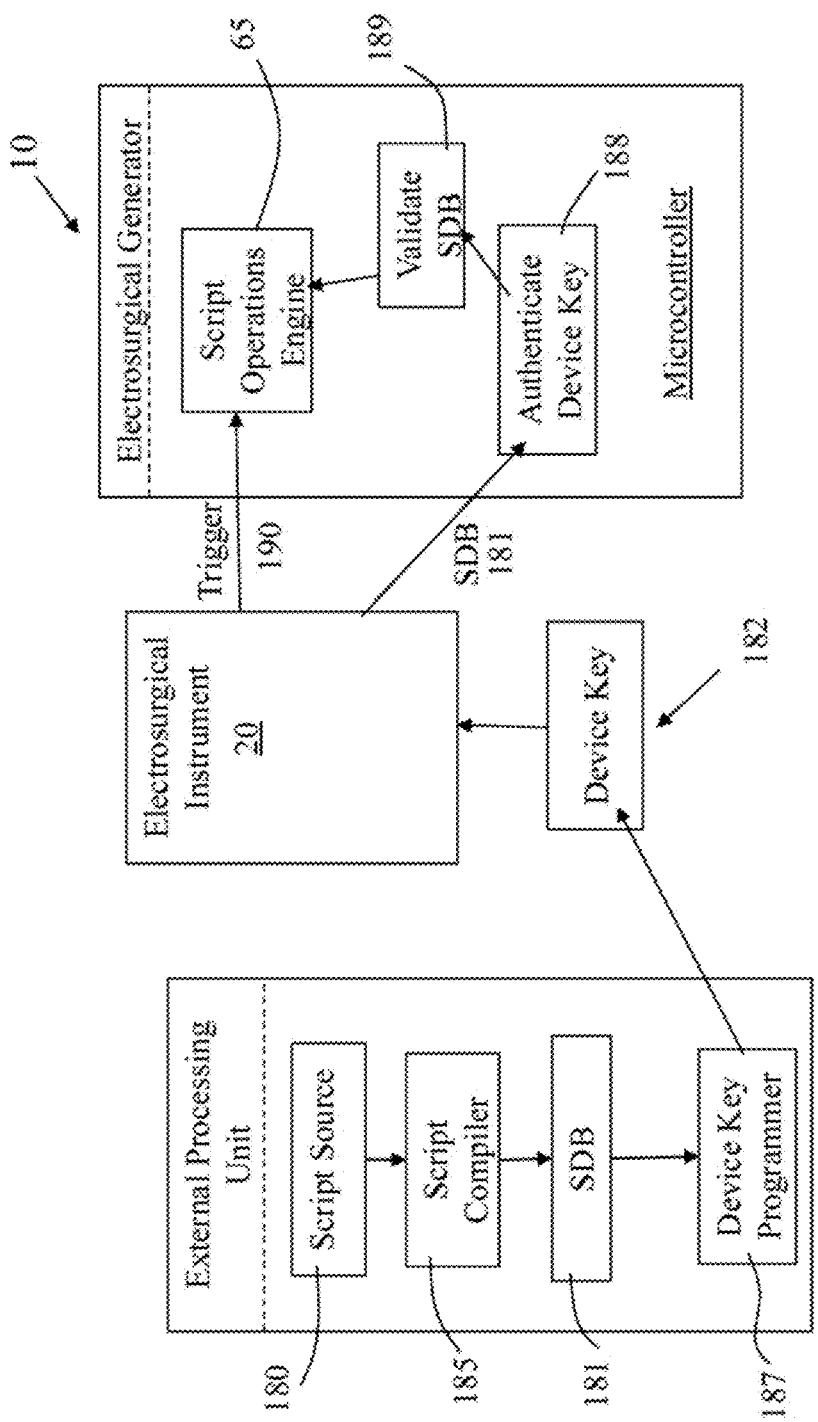
FIG. 18 is a schematic block diagram of portions of an electrosurgical system in accordance with various embodiments of the present invention.

Referring to FIG. 18, the generator 10 receives script information from the electrosurgical device or instrument 20 when the device is connected. The generator uses this script information to define a number of states and the order of execution of the states.

The script source file or script information 180 written by the device script author and not resident on the instrument or the generator 10 is text or user readable. The script information is compiled using a script complier 185 to generate a device script database or binary file (SDB) 101. The script binary file is transferred by a device key programmer 187 to a memory module that is connectable or incorporated into the electrosurgical instrument 20 via a device key 182. As the electrosurgical instrument is connected to the electrosurgical generator, the generator authenticates the script binary file and/or the instrument (188). The generator validates the script binary file (189) and if validated the operations engine utilizes the script initiated by the actuation by the connected instrument (190). Script source file in one embodiment is a text file containing a device script that is specific for a specific electrosurgical instrument, generator and/or surgical procedure. The script source file for a device in one embodiment includes information containing parameters and a script (states, functions, events) for the electrosurgical generator and/or electrosurgical instrument. After successful validation, the script compiler assembles data into a binary format that defines a state machine for use by the electrosurgical generator. Script compiler as shown in FIG. 18 in one embodiment is separate from the electrosurgical generator and is responsible for reading in text from the script source file and validating its contents.

When the memory module is inserted into the generator, the generator downloads a binary file that is stored in a ferromagnetic random access memory (FRAM) or microcontroller disposed within the module. The binary includes logic for implementing the treatment algorithms or processes in accordance with various embodiments. The generator in various embodiments includes firmware/software, hardware or combinations thereof responsible for processing the binary to authentic the connected instrument and to execute the binary for performing the treatment algorithm. In this manner, the generator is configured to operate only with authenticated, compatible hand tools.

In one embodiment, instrument scripts or script database represent an instrument process for a specific or given instrument. The instrument scripts are stored on memory connected to or integrated with an instrument, the controller or a combination thereof. The event handler responds to specific events, such as a switch activation/de-activation, instrument positions or exceeding measurement thresholds. The operations engine based on the detected event if appropriate for a given event provides output to the connected instrument. In one embodiment, an event is a discrete change, as in a switch is asserted or de-asserted.

Script state is a block or set of script functions or operation conditions and script events or indicators. Script functions are configurable instructions for controlling the generator and/or the instruments. Script operators are logical and comparison operations performed during a script event evaluation. Script parameters are configuration data used by all states and events of a script and in one embodiment are declared in their own dedicated section of the script file. Script events are a discrete change in an electrosurgical generator measurement. When a Script Event occurs, for example, a sequence of script functions is executed.

In accordance with various embodiments, phase angle between voltage and current and/or the change or phase angle rate is utilized to maximize the amount of time the tissue is in a predetermined temperature range. In one embodiment, the predetermined temperature range is between 60 degrees C. to 100 degrees C. In one embodiment, low voltage is utilized to minimize temperature effects while accelerating sealing or fusing time.

In accordance with various embodiments, tissue is grasped between jaws of the bipolar electrosurgical device. The bipolar electrosurgical device removably connected to an electrosurgical generator is supplied RF energy that upon command is supplied to the tissue. The supplied RF energy has a predetermined voltage range that heats the tissue at a predetermined rate. In one embodiment, the predetermined voltage range is between 20 Vrms to 50 Vrms. During the application of RF energy, the phase angle between output voltage and current are monitored to identify phase increases or decreases. Initially, phase angle is monitored to determine a change in phase angle or rate from increasing to decreasing. It is contemplated that once this point of inflection has occurred, it is determined that water in the jaws of the device has reached 100 degrees C. and the temperature to cause the required tissue affect has been exceeded. A shutoff point is then determined to terminate the supply of RF energy.

Figure 19:
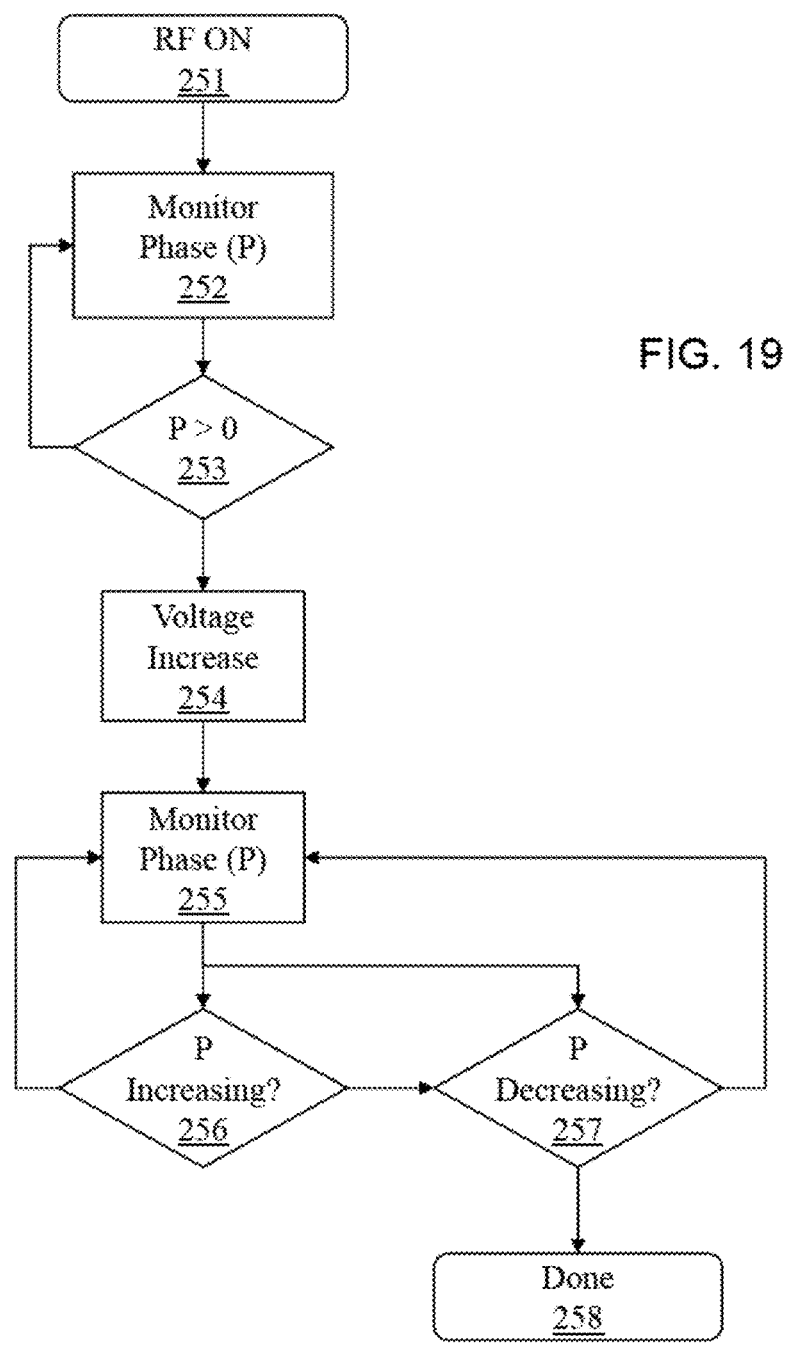
FIG. 19 is a flow chart illustrating operations of an electrosurgical system in accordance with various embodiments of the present invention.
Figure 20:
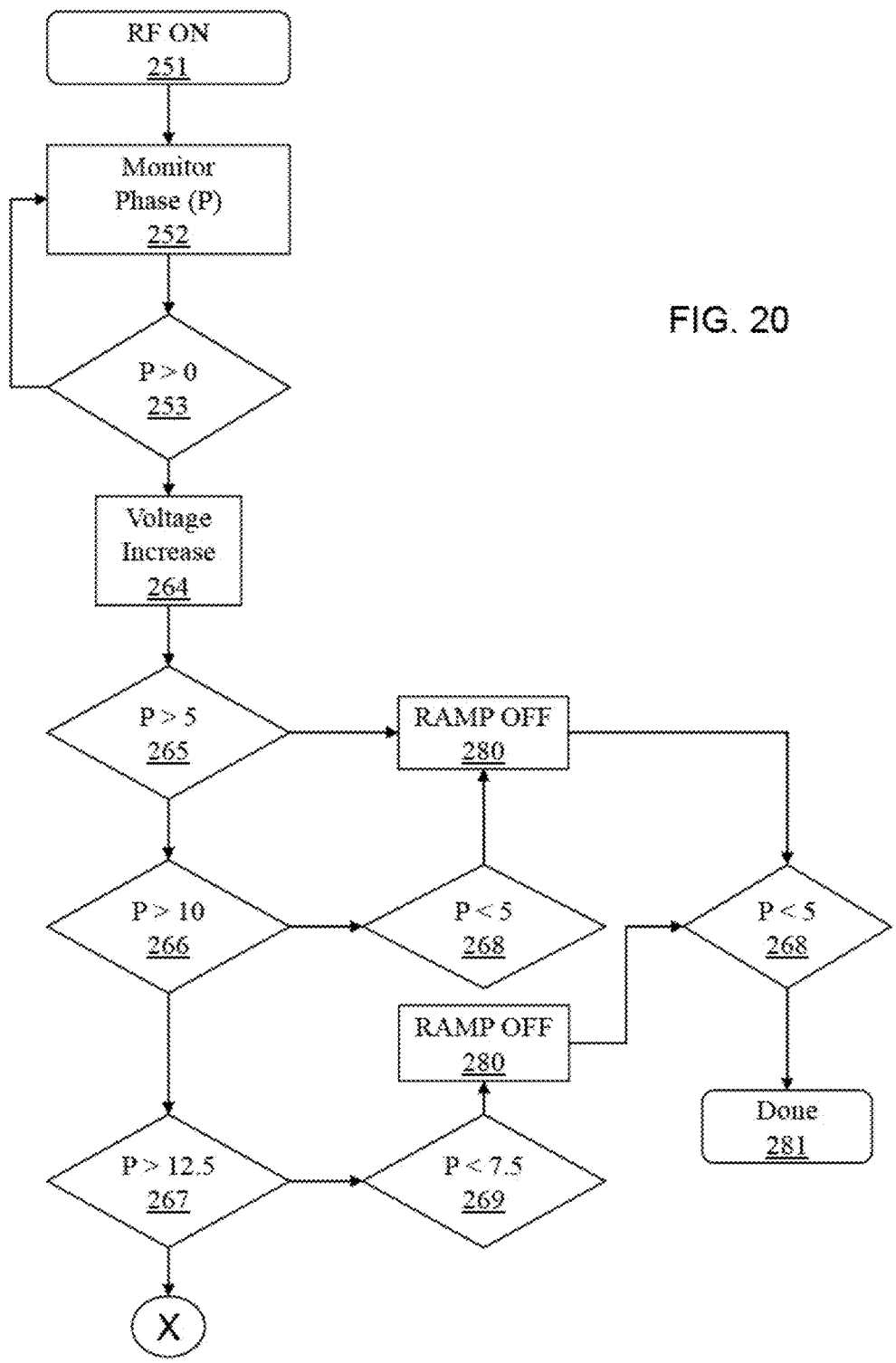
FIG. 20 is a flow chart illustrating operations of an electrosurgical system in accordance with various embodiments of the present invention.
Figure 21:
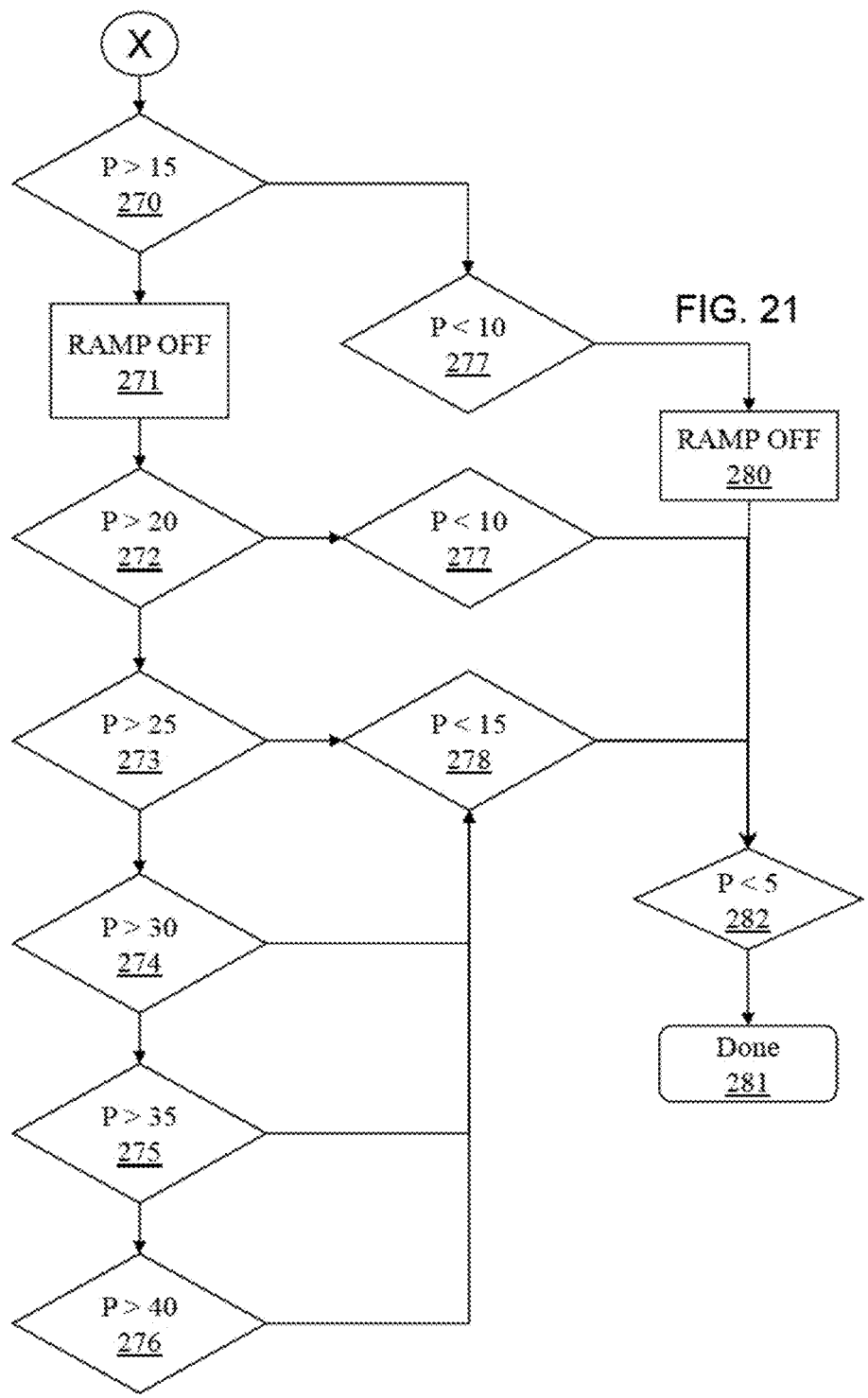
FIG. 21 is a flow chart illustrating operations of an electrosurgical system in accordance with various embodiments of the present invention.

Exemplary RF energy control process for the electrosurgical generator and associated electrosurgical tool for fusing tissue in accordance with various embodiments are shown in FIGS. 19-21. In various embodiments, as illustrated in FIG. 19, RF energy is supplied by the generator through the connected electrosurgical tool (251). The generator monitors at least the phase and/or change/rate of phase of the supplied RF energy (252). If a phase/phase change is greater than zero or trending positive (253), voltage is increased (254). The generator continues to monitor at least the phase and/or change/rate of phase of the supplied RF energy (255). If the phase/phase change continues to increase (256), the generator continues to monitor the phase and/or change of phase. If the phase/phase change decreases (257), the process is done or termination procedures are initiated and/or RF energy supplied by the generator is stopped (258).

In one embodiment, prior to the start of the process, impedance is measured to determine a short or open condition through a low voltage measurement signal delivered to a connected electrosurgical tool. In one embodiment, passive impedance is measured to determine if the tissue grasped is within the operating range of the electrosurgical tool (2-200Ω). If the initial impedance check is passed, RF energy is supplied to the electrosurgical tool. After which impedance/resistance is not measured or ignored.

Initially, initial parameters are set to prepare for sealing of tissue grasped between the jaws. In one embodiment, voltage and current settings are set to a specific setting. In one embodiment, voltage of the RF energy is applied in a ramping fashion starting from 30% of a global setting or user selected level (e.g., 27.5-88V for level 1, 25.0-80V for level 2 and 22.5V-72V for level 3). The voltage DAC is set to 30% of the voltage setting which on level 2 (medium) is 25.5 Vrms. The phase is monitored to determine a phase angle above zero degrees and to heat the tissue and water between the jaws of the electrosurgical device at a predetermined slow rate.

Referring now to FIGS. 20-21, in various embodiments, RF energy is supplied by the generator through the connected electrosurgical tool (251). The generator monitors at least the phase and/or change/rate of phase of the supplied RF energy (252). If a phase/phase change is greater than zero or trending positive (253), voltage is increased (254). In various embodiments, voltage is increased at a predetermined rate, for example, 50% over 5 seconds, which is 42.5 Vrms on level 2 (medium) after the phase has increased to be greater than zero degrees. The ramping continues until a predetermined condition is met. In one embodiment, the ramping continues as the monitored phase angle increases to above five degrees. This ensures that phase is increasing as expected based on heating of the tissue.

In a next subsequent state (265), if the monitored phase angle increases above a predetermined phase value, e.g., 5 degrees, phase continues to be monitored for an increasing state or condition. This is contemplated that such an increasing condition is an indication that the temperature of the tissue and water between the jaws is increasing but less than 100 degrees C. However, the monitored phase indicating a decreasing state or condition provides a different indication. It is contemplated that such an indication is that the temperature of the tissue and water between the jaws has reached at least 100 degrees C. and/or the desired tissue affect has been completed, e.g., sealing and/or cutting of the tissue.

In one or more subsequent states, the monitored phase angle is checked for an increasing or decreasing condition. In accordance with various embodiments, various incremental or periodic checks are performed along with various incremental or periodic updates to various predetermined thresholds or indications to determine an increasing phase angle or rates of change condition or a decreasing phase angle or rates of change condition.

When one or more of the subsequent states determines that the phase angle, rate or trend of the phase angle is decreasing rather than increasing, the indication is that the desired tissue affect has been completed, e.g., sealing and/or cutting of the tissue. As such, it is contemplated that in such an indication the temperature of the tissue and water between the jaws has reached at least 100 degrees C.

At such a state or in a subsequent state, voltage ramping or increasing of the output RF energy is ramped down or decreased. As such, the rapid boiling of water is reduced or prevented and temperature is held steady or constant until a predetermined condition is reached. In one embodiment, the predetermined condition is the phase angle dropping to at least 5 degrees.

In accordance with various embodiments, in a next subsequent state (266), if the monitored phase angle increases above a predetermined phase value, e.g., 10 degrees, phase continues to be monitored for an increasing state or condition. If however the monitored phase angle instead indicates a decreasing state, e.g., decreases below a predetermined phase value, e.g., five degrees (268) or a predetermined time limit has been reached, voltage increase is stopped (280). Subsequently, if the monitored phase angle continues to indicate a decreasing state, e.g., decreases below a predetermined phase value, e.g., five degrees (268) or if a predetermined time limit has been reached, RF energy is stopped and the process ends (281).

If the monitored phase angle indicates an increasing state, e.g., in a next subsequent state (267), if the monitored phase angle increases above a predetermined phase value, e.g., 12.5 degrees, phase continues to be monitored for a continued increasing state or condition. If the monitored phase angle instead now indicates a decreasing state, e.g., decreases below a predetermined phase value, e.g., 7.5 degrees (269) or a predetermined time limit has been reached, voltage increase is stopped (280). Subsequently, if the monitored phase angle continues to indicate a decreasing state, e.g., decreases below a predetermined phase value, e.g., five degrees (268) or if a predetermined time limit has been reached, RF energy is stopped and the process ends (281).

In a next subsequent state (270), if the monitored phase angle indicates an increasing state, e.g., increases above a predetermined phase value, e.g., 15 degrees, voltage increase is stopped (271) and phase continues to be monitored for an increasing state or condition. If however the monitored phase angle instead indicates a decreasing state, e.g., decreases below a predetermined phase value, e.g., ten degrees (277) or a predetermined time limit has been reached, voltage increase is stopped (280). Subsequently, if the monitored phase angle continues to indicate a decreasing state, e.g., decreases below a predetermined phase value, e.g., five degrees (282) or if a predetermined time limit has been reached, RF energy is stopped and the process ends (281). In a next subsequent state (272), if the monitored phase angle indicates an increasing state, e.g., increases above a predetermined phase value, e.g., 20 degrees, phase continues to be monitored for an increasing state or condition. If the monitored phase angle instead indicates an decreasing state, e.g., decreases below a predetermined phase value, e.g., ten degrees (277) or a predetermined time limit has been reached, phase continues to be monitored for a decreasing state or condition. Subsequently, if the monitored phase angle decreases below a predetermined phase value, e.g., five degrees (282) or if a predetermined time limit has been reached, RF energy is stopped and the process ends (281).

In a next subsequent state (273), if the monitored phase angle continues to indicate an increasing state, e.g., increases above a predetermined phase value, e.g., 25 degrees, phase continues to be monitored for an increasing state or condition. If the monitored phase angle decreases instead below a predetermined phase value, e.g., fifteen degrees (278) or a predetermined time limit has been reached, phase continues to be monitored for a decreasing state or condition. Subsequently, if the monitored phase angle decreases below a predetermined phase value, e.g., five degrees (282) or if a predetermined time limit has been reached, RF energy is stopped and the process ends (281). In a next subsequent state (274), if the monitored phase angle increases above a predetermined phase value, e.g., 30 degrees, phase continues to be monitored for an increasing state or condition. If the monitored phase angle instead decreases below a predetermined phase value, e.g., fifteen degrees (278) or a predetermined time limit has been reached, phase continues to be monitored for a decreasing state or condition. Subsequently, if the monitored phase angle decreases below a predetermined phase value, e.g., five degrees (285) or if a predetermined time limit has been reached, RF energy is stopped and the process ends (281).

In a next subsequent state (275), if the monitored phase angle increases above a predetermined phase value, e.g., 35 degrees, phase continues to be monitored for an increasing state or condition. However, if the monitored phase angle instead decreases below a predetermined phase value, e.g., fifteen degrees (278) or a predetermined time limit has been reached, phase continues to be monitored for a decreasing state or condition. Subsequently, if the monitored phase angle decreases below five degrees (282) or if a predetermined time limit has been reached, RF energy is stopped and the process ends (281). In a next subsequent state (276), if the monitored phase angle increases above a predetermined phase value, e.g., 40 degrees, phase is monitored for a decreasing condition and if the monitored phase angle decreases below a predetermined phase value, e.g., fifteen degrees (278) or a predetermined time limit has been reached, phase continues to be monitored for a decreasing state or condition. Subsequently, if the monitored phase angle decreases below a predetermined phase value, e.g., five degrees (282) or if a predetermined time limit has been reached, RF energy is stopped and the process ends (281). It is contemplated and noted that, for the exemplary and operational seal/fuse and cut/dissection process or system provided above and throughout the application, the frequency of incremental checks and/or the indications of increasing or decreasing states, e.g., predetermined angles or rates of change, can vary to provide different and various levels and granularity of regulation or control as desired or required based on the specific electrosurgical instrument, generator, tissue and/or surgical procedure.

Figure 23:
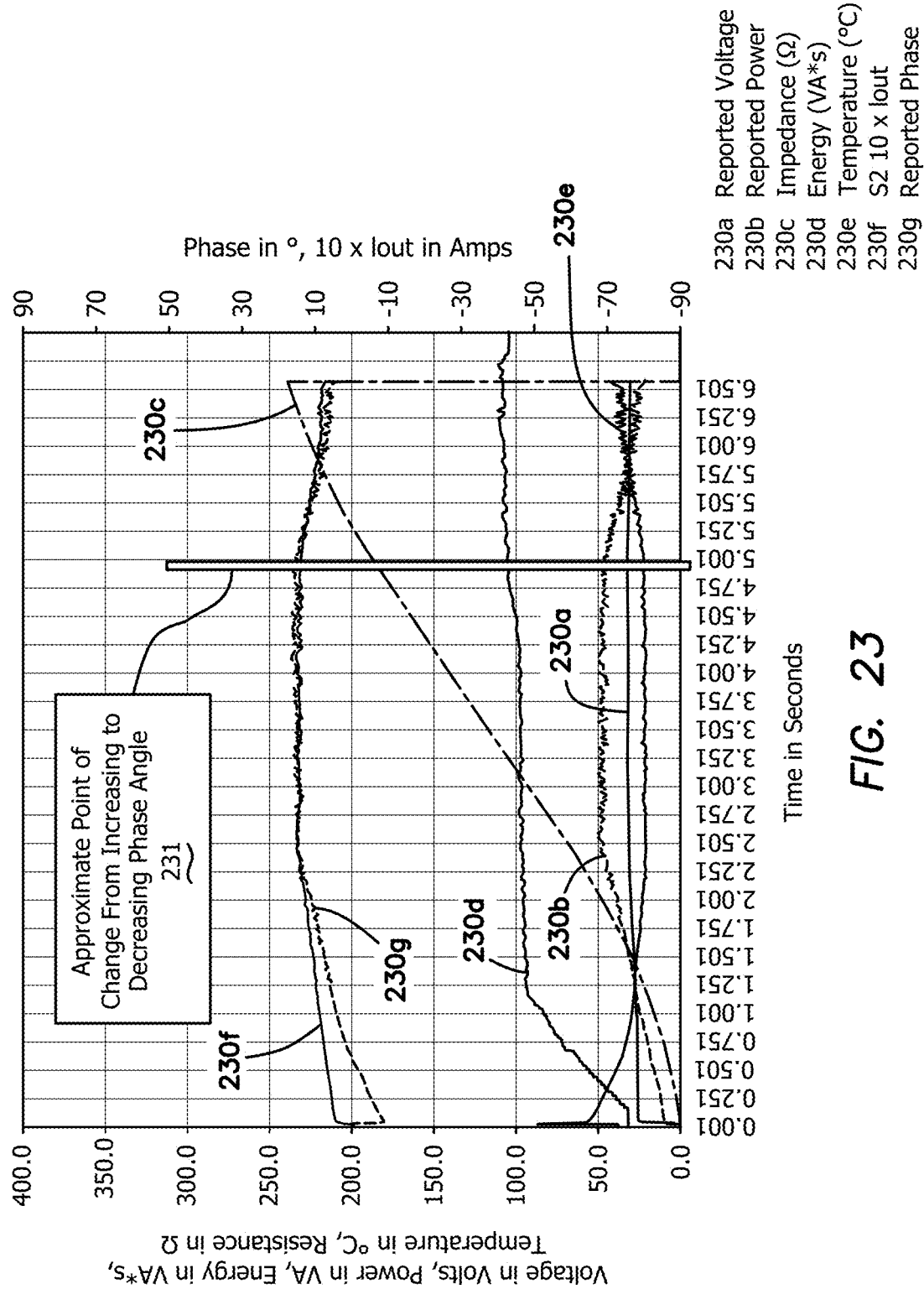
FIG. 23 is a graphical representation of samples of experimental data for an electrosurgical system in accordance with various embodiments of the present invention.
Figure 24:
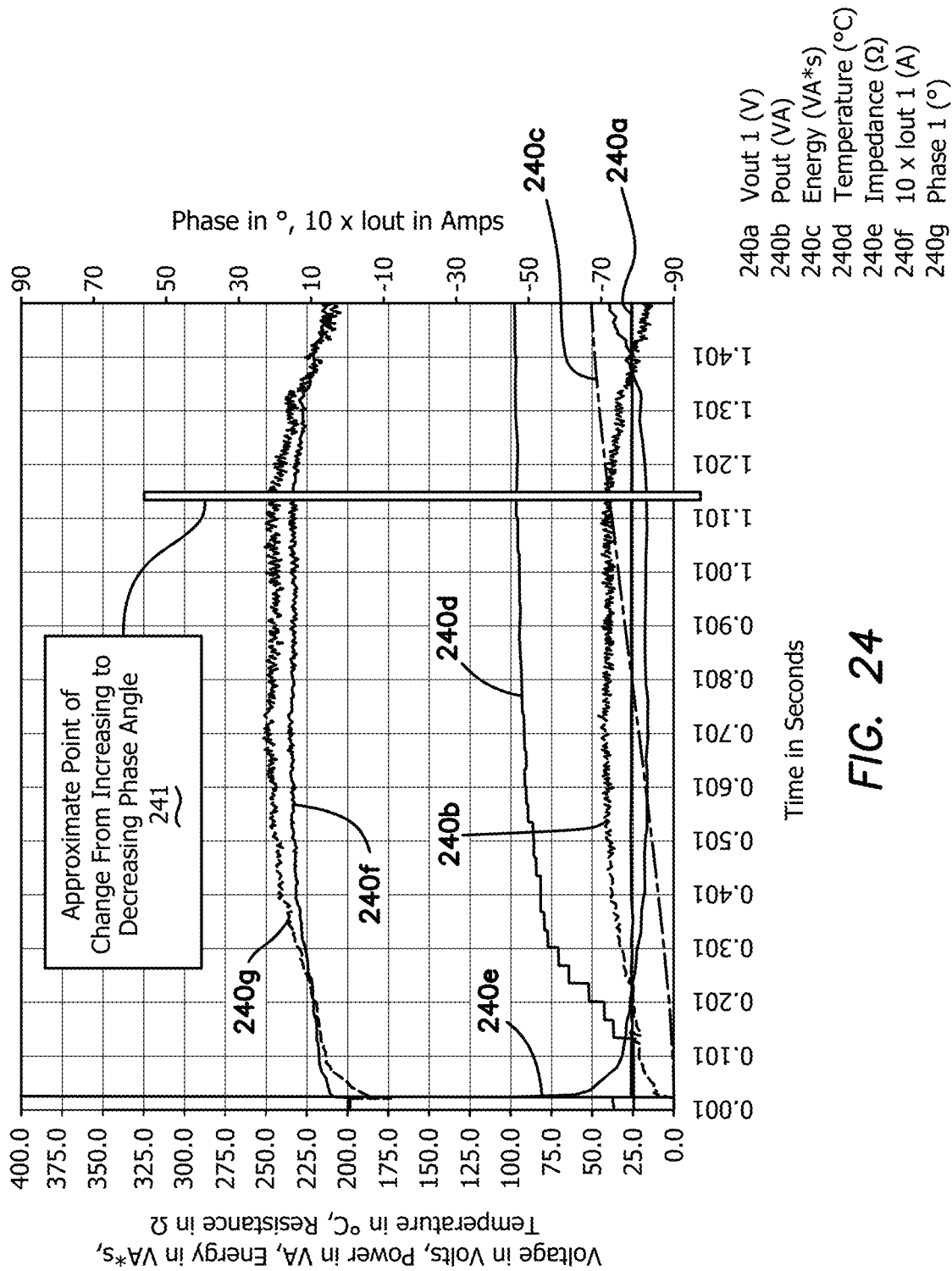
FIG. 24 is a graphical representation of samples of experimental data for an electrosurgical system in accordance with various embodiments of the present invention.

FIGS. 22-24 are graphical representations of exemplary vessel sealing/fusing utilizing systems and processes in accordance with various embodiments of the present invention. As shown, the success rate 223 of providing a tissue seal above 3× systolic burst pressure are high and time 223 for sealing of vessels up to 4 mm in size was small, e.g., less than 2 seconds. The times for sealing vessels between 4-7 mm was also reduced, e.g., less than 5 seconds. The time for the phase angle to decrease from the maximum to a predetermined phase value, e.g., 5 degrees, is longer than those up to 4 mm. Such changes or reduction in sealing time while also providing successful vessel seals, e.g., withstanding above 3× systolic burst pressure, in accordance with various embodiments is refined by identifying and/or triggering at the point of inflection of the derivate of the phase trend and incorporated into incremental checks, state indicators or thresholds. In various embodiments, the point of inflection of the derivate of the phase trend is identified at the point where the phase trend changes from an increasing state to a decreasing state.

As shown in FIG. 23, the vessel was 6.62 mm in diameter and was successfully sealed, e.g., having a burst pressure of 12.7 psi. Additionally, as shown, the phase angle $230g$ increases as RF energy is applied. The rate of the increase is not rapid but rather sufficiently slow as well as the temperature $230d$ of the tissue. The point of inflection $231$, e.g., the point at which phase changes from increasing to decreasing occurs approximately 1.5 seconds before RF energy is stopped. As shown in FIG. 24, the vessel was 1.89 mm in diameter and was successfully sealed, e.g., having a burst pressure of 13 psi. The overall trend of phase angle $240g$ and temperature $240d$ is similar as with the previous vessel seal, although the time scale shown in FIG. 24 is approximately ¼ of that of FIG. 23. Also, as illustrated, phase $230g$, $240g$ are shown relative to other tissue readings or indicators such as voltage $230a$, $240a$; power $230b$, $240b$; impedance $230e$, $240e$; energy $230c$, $240c$; temperature $230d$, $240d$; and current $230f$, $240f$. Additionally, although shown in FIGS. 23-24, in various embodiments, the generator is configured to not measure or calculate one or more of the indicators or readings, e.g., temperature or energy, to reduce operational and power costs and consumptions and the number of parts for the generator. The additional information or readings are generally provided or shown for context purposes.

It is noted that the impedance of the tissue is near its minimum for the entire seal cycle. As such, this provides a low voltage and high current and thus consistent power delivery throughout the seal cycle. Efficient or consistent power delivery reduces thermal spread. In accordance with various embodiments, the time for sealing can be decreased, reduction in voltage output to below 50 Vrms and/or reduction of power output to below 50 Watts. To avoid false readings, in accordance with various embodiments, the electrosurgical generator does not measure resistance or impedance of the tissue during the supply of RF energy to the tissue.

In accordance with various embodiments, an electrosurgical system is provided that decreases thermal spread, provides lower output levels and efficient power delivery for sealing vessels or tissue in contact with a bipolar electrosurgical instrument through the controlled and efficient supply of RF energy.

As described throughout the application, the electrosurgical generator ultimately supplies RF energy to a connected electrosurgical instrument. The electrosurgical generator ensures that the supplied RF energy does not exceed specified parameters and detects faults or error conditions. In various embodiments, an electrosurgical instrument provides the commands or logic used to appropriately apply RF energy for a surgical procedure. An electrosurgical instrument for example includes memory having commands and parameters that dictate the operation of the instrument in conjunction with the electrosurgical generator. For example, in a simple case, the generator can supply the RF energy but the connected instrument decides how much or how long energy is applied. The generator however does not allow the supply of RF energy to exceed a set threshold even if directed to by the connected instrument thereby providing a check or assurance against a faulty instrument command.

Turning now to some of the operational aspects of the electrosurgical tool or instrument described herein in accordance with various embodiments, once a vessel or tissue bundle has been identified for fusing, dissecting or both, the first and second jaws are placed around the tissue. The movable handle 23 is squeezed moving the movable handle proximally with respect to the stationary housing 28. As the movable handle moves proximally the first jaw pivots towards the second jaw effectively clamping the tissue. Radio frequency energy is applied to the tissue by depressing the activation button on the stationary handle. Once the tissue has been fused, dissected or both, the movable handle is re-opened.

Alternatively or additionally, with the jaws in a fully open position or in an intermediate position between a fully open position and the engaged position, radio frequency energy can applied to the tissue in contact with a lower surface or portion of the lower jaw by depressing the activation button or a separate activation button to fuse and/or dissect tissue.

As described generally above and described in further detail below, various electrosurgical instruments, tools or devices can be used in the electrosurgical systems described herein. For example, electrosurgical graspers, scissors, tweezers, probes, needles, and other instruments incorporating one, some, or all of the aspects discussed herein can provide various advantages in an electrosurgical system. Various electrosurgical instruments and generator embodiments and combinations thereof are discussed throughout the application. It is contemplated that one, some, or all of the features discussed generally throughout the application can be included in any of the embodiments of the instruments, generators and combinations thereof discussed herein. For example, it can be desirable that each of the instruments described include a memory for interaction with the generator as previously described and vice versa. However, in other embodiments, the instruments and/or generators described can be configured to interact with a standard bipolar radio frequency power source without interaction of an instrument memory. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Likewise, such software components may be interchanged with hardware components or a combination thereof and vice versa.

Further examples of the electrosurgical unit, instruments and connections there between and operations and/or functionalities thereof are described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; and Ser. No. 12/416,128, filed Mar. 31, 2009, entitled "Electrosurgical System"; the entire disclosures of which are hereby incorporated by reference as if set in full herein. Certain aspects of these electrosurgical generators, tools and systems are discussed herein, and additional details and examples with respect to various embodiments are described in US Provisional Application Nos. 61/994, 215, filed May 16, 2014, entitled "Electrosurgical Fusion Device"; 61/944,185, filed May 16, 2014, "Electrosurgical Generator with Synchronous Detector"; 61/994,415, filed May 16, 2014, "Electrosurgical System"; and 61/944,192, filed May 16, 2014, entitled "Electrosurgical Generator", the entire disclosures of which are hereby incorporated by reference as if set in full herein.

The above description is provided to enable any person skilled in the art to make and use the surgical instruments and perform the methods described herein and sets forth the best modes contemplated by the inventors of carrying out their inventions. Various modifications, however, will remain apparent to those skilled in the art. It is contemplated that these modifications are within the scope of the present disclosure. Additionally, different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth. Also, embodiments of the present invention should be considered in all respects as illustrative and not restrictive.

The invention claimed is:

1. An electrosurgical system comprising:
an electrosurgical instrument comprising:
a first jaw comprising a first electrode; and
a second jaw opposing the first jaw and comprising a second electrode, the first and second jaws pivotably arranged to grasp tissue between the first and second jaws and the first and second electrodes of the first and second jaws being arranged to transmit radio frequency energy (RF) between the first and second electrodes;
an electrosurgical generator arranged to supply the radio frequency (RF) energy, the electrosurgical generator comprising a controller arranged to periodically monitor a phase angle of the supplied RF energy and configured to signal an RF amplifier to increase voltage of the supplied RF energy when the monitored phase angle is greater than zero and increasing.

2. The electrosurgical system of claim 1 wherein the controller continues to signal the RF amplifier to increase voltage of the RF energy when the monitored phase angle continues to exceed a predetermined threshold angle and the RF amplifier increases voltage of the supplied RF energy at a predetermined constant rate.

3. The electrosurgical system of claim 2 wherein the controller is configured to signal the RF amplifier to halt the supplied RF energy when the monitored phase angle decreases.

4. The electrosurgical system of claim 2 wherein the controller periodically monitors a rate of change of the phase angle of the supplied RF energy and the controller signals the RF amplifier to halt the supplied RF energy when the rate of change of the phase angle falls below a predetermined threshold rate.

5. The electrosurgical system of claim 1 wherein the RF amplifier increases voltage of the supplied RF energy at a predetermined constant rate and the controller signals the RF amplifier to halt the voltage increase of the supplied RF energy when the monitored phase angle exceeds a predetermined threshold angle while the RF amplifier continues to supply RF energy.

6. The electrosurgical system of claim 5 further comprising RF sense circuitry arranged to measure voltage and current of the supplied RF energy by using analog circuitry, the measured voltage and current used to calculate the monitored phase angle monitored.

7. The electrosurgical system of claim 1 wherein the first jaw further comprises a third electrode and the second jaw further comprises a fourth electrode.

8. The electrosurgical system of claim 7 wherein the first and second electrodes are arranged to fuse the tissue between the first and second jaws using radio frequency energy on one side of a longitudinal axis and the third and fourth electrodes are arranged to fuse the tissue between the first and second jaws using radio frequency energy on an opposing side of the longitudinal axis.

9. The electrosurgical system of claim 8 wherein the second electrode protrudes up towards the first jaw to a first inner flat portion of the second electrode and the fourth electrode protrudes up towards the first jaw to a second inner flat portion of the fourth electrode adjacent to the first inner flat portion of the second electrode.

10. The electrosurgical system of claim 9 wherein the second jaw further comprises a fifth electrode extending away from the first jaw and the second jaw.

11. The electrosurgical system of claim 10 wherein the fifth electrode is arranged to cut the tissue outside the second jaw through radio frequency energy being conducted between the fifth electrode and the second and fourth electrodes.

12. The electrosurgical system of claim 7 wherein the first electrode is arranged to have a first polarity and the second electrode is arranged to have a second polarity, the second polarity being different from the first polarity of the first electrode.

13. The electrosurgical system of claim 12 wherein the fourth electrode is arranged to have the first polarity and the third electrode is arranged to have the second polarity and wherein the first, second, third and fourth electrodes electrically interact together to fuse and cut the tissue between the first and second jaws.

14. The electrosurgical system of claim 7 wherein the second electrode has a flat portion and the fourth electrode has a flat portion.

15. The electrosurgical system of claim 14 wherein the first electrode has an angled surface and the third electrode has an angled surface.

16. The electrosurgical system of claim 7 wherein the second electrode protrudes up towards the first jaw to a first inner flat portion of the second electrode and the fourth electrode protrudes up towards the first jaw to a second inner flat portion of the fourth electrode adjacent to the first inner flat portion of the second electrode.

17. The electrosurgical system of claim 16 wherein the second jaw further comprises a fifth electrode extending away from the first jaw and the second jaw.

18. The electrosurgical system of claim 17 wherein the fifth electrode is arranged to cut the tissue outside the second jaw through radio frequency energy being conducted between the fifth electrode and the second and fourth electrodes.

* * * * *